(12) United States Patent
Williams, III et al.

(10) Patent No.: US 12,226,404 B2
(45) Date of Patent: *Feb. 18, 2025

(54) METHODS FOR MAKING COMPOSITIONS FOR PULMONARY ADMINISTRATION

(71) Applicant: Board of Regents, the University of Texas System, Austin, TX (US)

(72) Inventors: Robert O. Williams, III, Austin, TX (US); Keith P. Johnston, Austin, TX (US); Prapasri Sinswat, Austin, TX (US); Jason T. McConville, Austin, TX (US); Robert Talbert, San Antonio, TX (US); Jay I. Peters, San Antonio, TX (US); Alan B. Watts, Austin, TX (US); True L. Rogers, Midland, MI (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/836,067

(22) Filed: Jun. 9, 2022

(65) Prior Publication Data

US 2023/0040283 A1   Feb. 9, 2023

Related U.S. Application Data

(63) Continuation of application No. 16/294,885, filed on Mar. 6, 2019, now Pat. No. 11,382,899, which is a continuation of application No. 14/621,337, filed on Feb. 12, 2015, now Pat. No. 10,231,955, which is a continuation of application No. 12/522,774, filed as application No. PCT/US2008/050795 on Jan. 10, 2008, now Pat. No. 9,044,391.

(60) Provisional application No. 60/884,383, filed on Jan. 10, 2007.

(51) Int. Cl.

| | |
|---|---|
| A61K 31/436 | (2006.01) |
| A61K 9/00 | (2006.01) |
| A61K 9/16 | (2006.01) |
| A61K 9/19 | (2006.01) |
| A61K 9/51 | (2006.01) |
| A61K 38/13 | (2006.01) |
| A61P 11/00 | (2006.01) |
| A61P 37/00 | (2006.01) |
| A61P 37/06 | (2006.01) |

(52) U.S. Cl.
CPC .......... *A61K 31/436* (2013.01); *A61K 9/0075* (2013.01); *A61K 9/0078* (2013.01); *A61K 9/1623* (2013.01); *A61K 9/1694* (2013.01); *A61K 9/19* (2013.01); *A61K 9/5161* (2013.01); *A61K 9/5192* (2013.01); *A61K 38/13* (2013.01)

(58) Field of Classification Search
CPC .. A61K 31/436; A61K 9/0075; A61K 9/0078; A61K 9/1623; A61K 9/1694; A61K 38/13; A61P 11/00; A61P 37/00; A61P 37/06

See application file for complete search history.

(56) References Cited

U.S. PATENT DOCUMENTS

| | | | |
|---|---|---|---|
| 4,894,366 A | 1/1990 | Okuhara et al. | |
| 5,260,301 A | 11/1993 | Nakanishi et al. | |
| 5,514,686 A | 5/1996 | Mochinzuki et al. | |
| 5,643,901 A | 7/1997 | Honbo et al. | |
| 5,648,351 A | 7/1997 | Kelly et al. | |
| 5,939,427 A | 8/1999 | Kagayama et al. | |
| 6,333,334 B1 | 12/2001 | Koshika | |
| 6,346,537 B1 | 2/2002 | Hata et al. | |
| 6,384,073 B1 | 5/2002 | Sakuma | |
| 6,440,458 B1 | 8/2002 | Yamashita et al. | |
| 6,447,806 B1 | 9/2002 | Gassmann et al. | |
| 6,524,556 B2 | 2/2003 | Murata et al. | |
| 6,835,396 B2 | 12/2004 | Brynjelsen et al. | |
| 6,865,890 B2 | 3/2005 | Williams et al. | |
| 6,946,117 B1 * | 9/2005 | Schutt ................... A61K 9/008 424/490 |
| 7,011,680 B2 | 3/2006 | Alt | |
| 7,087,237 B2 | 8/2006 | Peyman | |

(Continued)

FOREIGN PATENT DOCUMENTS

| | | |
|---|---|---|
| CA | 2590675 | 6/2006 |
| EP | 1036562 | 9/2000 |

(Continued)

OTHER PUBLICATIONS

Overhoff, Kirk Alan. "Improved oral bioavailability of poorly water soluble drugs using rapid freezing processes." (2006). (Year: 2006).*
"Aqueous", *Merriam Webster Collegiate Dictionary*, 10$^{th}$ Ed., pp. 58, Merriam-Webster, Inc.: Springfield, Massachusetts, 1996.
Arima et al., "Comparative Studies of the Enhancing Effects of Cyclodextrins on the Solubility and Oral Bioavailability of Tacrolimus in Rats", *Journal of Pharmaceutical Sciences*, 90(6): 690-701, 2001.
Arima et al., "Contribution of P-Glycoprotein to the Enhancing Effects of Dimethyl-B-Cyclodextrin on Oral Bioavailability of Tacrolim", *The Journal of Pharmacology and Experimental Therapeutics*, 297:547-555, 2001.

(Continued)

*Primary Examiner* — Abigail Vanhorn
(74) *Attorney, Agent, or Firm* — Parker Highlander PLLC

(57) ABSTRACT

The present invention includes compositions and methods for making and using a rapid dissolving, high potency, substantially amorphous nanostructured aggregate for pulmonary delivery of tacrolimus and a stabilizer matrix comprising, optionally, a polymeric or non-polymeric surfactant, a polymeric or non-polymeric saccharide or both, wherein the aggregate comprises a surface area greater than 5 m$^2$/g as measured by BET analysis and exhibiting supersaturation for at least 0.5 hours when 11-15-times the aqueous crystalline solubility of tacrolimus is added to simulated lung fluid.

9 Claims, 5 Drawing Sheets

(56) References Cited

U.S. PATENT DOCUMENTS

| | | | |
|---|---|---|---|
| 7,645,876 | B2 | 1/2010 | Keri et al. |
| 9,044,391 | B2 | 6/2015 | Williams et al. |
| 10,231,955 | B2 | 3/2019 | Williams et al. |
| 2002/0006901 | A1 | 1/2002 | Iacono |
| 2002/0102294 | A1 | 8/2002 | Bosch et al. |
| 2002/0142050 | A1 | 10/2002 | Straub et al. |
| 2003/0041602 | A1 | 3/2003 | Williams et al. |
| 2003/0114384 | A1 | 6/2003 | Podolsky |
| 2004/0022861 | A1 | 2/2004 | Williams et al. |
| 2004/0137070 | A1 | 7/2004 | Scherzer et al. |
| 2006/0057213 | A1 | 3/2006 | Larhrib et al. |
| 2006/0177500 | A1 | 8/2006 | Shin et al. |
| 2006/0210638 | A1 | 9/2006 | Liversidge et al. |
| 2006/0287352 | A1 | 12/2006 | Holm et al. |
| 2007/0287675 | A1 | 12/2007 | Hitt et al. |
| 2009/0011009 | A1 | 1/2009 | Benita et al. |
| 2015/0224062 | A1 | 8/2015 | Williams et al. |

FOREIGN PATENT DOCUMENTS

| | | |
|---|---|---|
| WO | WO 2006/026502 | 3/2006 |
| WO | WO 2006/031664 | 3/2006 |
| WO | WO 2006/110802 | 10/2006 |
| WO | WO 2008/127746 | 10/2008 |

OTHER PUBLICATIONS

Bayer et al., "Effect of inhaled tacrolimus on ischemia reperfusion injury in rat lung transplant model", *The Journal of Thoracic and Cardiovascular Surgery*, 146(5): 1213-1219, 2013.

Blot et al., "Nebulized Cyclosporine for Prevention of Acute Pulmonary Allograft Rejection in the Rat: Pharmacokinetic and Histologic Study," *The Journal of Heart and Lung Transplantation*, 14(6): 1162-1172, 1995.

Bosquillon et al., "Influence of formulation excipients and physical characteristics of inhalation dry powders on their aerosolization performance," *J. Control. Release* 70:329-339, 2001.

Brambilla et al., "Modulation of Aerosol Clouds Produced by Pressurized Inhalation Aerosols", *International Journal of Pharmaceutics*, 186:53-61, 1999.

Canadas et al., "Characterization of Liposomal Tacrolimus in LUng Surfactant-Like Phospholipids and Evaluation of Its Immunosuppressive Activity," *Biochemistry*, (2004), 43:9926-9938.

Carroll et al., "Tacrolimus Ointment: The Treatment of atopic Dermatitis and other Inflammatory Cutaneous Disease," *Exper Opin. Pharmacother.*, (2004), 5(10):2127-2137.

Chakinala et al., "Critical Care Aspects of Lung Transplant Patients," *J. Intensive Care Med.*, (2002), 17:8-33.

Coren et al., "The use of cyclosporine in corticosteroid dependent asthma", *Archive of Diseases in Childhood*, 77: 522-523, 1997.

Crowder, Timothy M et al. "Fundamental effects of particle morphology on lung delivery: predictions of Stokes' law and the particular relevance to dry powder inhaler formulation and development." *Pharmaceutical research* vol. 19,3 (2002): 239-45.

Curran et al., "Tacrolimus in Patients with Rheumatoid Arthritis," *Drugs*, (2005), 65(7):993-1001.

Davies et al., "A novel method for assessing dissolution of aerosol inhaler products," *Int. J. Pharm.* Apr. 2003; 255:175-87.

De Boer et al., "Characterization of inhalation aerosols: a critical evaluation of cascade impactor analysis and laser diffraction technique", *Int. J. Pharm.* (2002) 249:219-231.

Deuse et al., "Mechanisms behind local immunosuppression using inhaled tacrolimus in preclinical modals of lung transplantation", *American Journal of Respiratory Cell and Molecular Biology*, 43: 403-412, 2010.

Eriksson et al., "Investigations into the Stabilization of Drugs by Sugar Glasses: III. The Influence of Various High-pH Buffers", *Pharm. Res.* (2003) 20:1437-1443.

Evans et al. Less Growth More Risk Lower Multiple. Black Book, *Pharmaceutica Quarterly*, 2002: pp. 201-210.

Evans et al., "Preparation of Nanostructured Particles of Poorly Water Soluble Drugs via a Novel Ultrarapid Freezing Technology," *American Chemical Society*, (2006), pp. 320-329.

Extended European Search report issued in European Application No. 087803672, dated Sep. 10, 2012, 5pp.

Fu et al., "New polymeric carriers for controlled drug delivery following inhalation or injection," *Biomaterials* (2002) 23:4425-4433.

Gao et al., "Enhanced Oral Bioavailability of a Poorly Water Soluble Drug PNU-91325 by Supersaturatable Formulations," *Drug Dev. Ind. Pharm.* (2004) 30:221-229.

Grenha et al., "Microencapsulated chitosan nanoparticles for lung protein delivery," *Eur. J. Pharm. Sci.* (2005) 25:427-437.

Griffies et al., "Topical 0.1 % Tacrolimus for the Treatment of Discoid Lupus Erythematosus and Pemphigus Erythematosus in Dogs," *J. Am. Anim. Hosp. Assoc.*, (2004), 40:29-41.

Grimm et al., "Superior prevention of acute rejection by tacrolimus vs. cyclosporine in heart transplant recipients—a large European trial", *American Journal of Transplantation*, 6:1387-1397, 2006.

Guglielmi et al., "Acute respiratory distress syndrome secondary to antisynthetase syndrome is reversible with tacrolimus", *Eur Respir J.*, 31: 213-217, 2008.

Gupta et al., "Tacrolimus: A Review of its Use for the Management of Dermatoses," *JEADV*, (2002), 16:100-114.

Hersperger et al., "A Locally Active Antiinflammatory Macrolide (MLD987) for Inhalation Therapy of Asthma," *J. Med. Chem.*, (2004) 47:4950-4957.

Hooks, "New Drug Developments: Tacrolimus, a New immunosuppressant—A Review of the Literature," *The Annals of Pharmacotherapy*, Apr. 1994, vol. 28, pp. 501-511.

Horita et al., "Tacrolimus and steroid treatment for acute exacerbation of idiopathic pulmonary fibrosis", *Inter Med.*, 50: 189-195, 2011.

Hu et al., "Stable amorphous danazol nanostructured powders with rapid dissolution rates produced by spray freezing into liquid," *Drug Dev. Ind. Pharm.* (2004) 30:695-704.

Iervolino et al., "Penetration enhancement of ibuprofen from supersaturated solutions through human skin," *Int. J. Pharm.* (2001) 212:131-141.

Ingu, "Effects of Inhaled FK 506 on the Suppression of Acute Rejection After Lung Transplantation: Use of a Rat Orthotopic Lung Transplantation Model," *The Journal of Heart and Lung Transplantation*, May 2005, pp. 538-543.

International Preliminary Report on Patentability for PCT/US2008/050795, dated Jul. 14, 2009, 9 pages.

International Search Report and Written Opinion for PCT/US2008/050795, dated May 16, 2008, 10 pages.

Jacobson et al., "Stability of Tacrolimus in an Extemporaneously Compounded Oral Liquid," *Am. J. Health Sys. Pharm.*, Jan. 15, 1997, vol. 54, pp. 178-180.

Jain et al., "Cyclosporin and Tacrolimus in Clinical Transplantation," *Clin. Immunother.*, May 1996, 5 (5):351-373.

Jusko et al., "Monitoring FK 506 Concentrations in Plasma and Whole Blood," *Transplantation Proceedings*, Dec. 1991, vol. 23, No. 6, pp. 2732-2735.

Jusko et al., "Pharmacokinetics of Tacrolimus in Liver Transplant Patients," *Clin. Pharma col. Ther.*, (1995) 57:281-290.

Kawashima, "Nanoparticulate systems for improved drug delivery," *Adv. Drug. Deliv. Rev.* (2001) 47:1-2.

Keenan et al., "Improved Immunosuppression with Aerosolized Cyclosporine in Experimental pulmonary Transplantation," *Transplantation*, Jan. 1992, vol. 53, No. 1, pp. 20-25.

Knoop et al., "Immunosuppressive therapy after human lung transplantation," *Eur. Respir. J.*, 23:159-171, 2004.

Lake et al., "The Impact of Immunosuppressive Regimens on the Cost of Liver Transplantation—Results from the UA FK506 Multicenter Trial," *Transplantation*, Nov. 27, 1995, vol. 60, No. 10, pp. 1089-1095.

Lampen et al., "Metabolism of the Immunosuppressant Tacrolimus in the Small Intestine: Cytochrome P450, Drug Interactions, and Interindividual Variability," *Drug Metabolism and Disposition*, vol. 23, No. 12, (1995), pp. 1315-1324.

(56) References Cited

OTHER PUBLICATIONS

Lamprecht et al., "Design of pH-Sensitive Microspheres for the Colonic Delivery of the Immunosuppressive Drug Tacrolimus," *European Journal of Pharmaceutics and Biophamaceutics*, (2004), 58:37-43.

Lamprecht et al., "FK506 Microparticles Mitigate Experimental Colitis with Minor Renal Calcineurin Suppression," *Pharmaceutical Research*, Feb. 2005, vol. 22, No. 2, pp. 193-199.

Lee et al., "Physiochemical, Pharmacokinetic and Pharmacodynamic Evaluation of Liposomal Tacrolimus (FK 506) in Rats," *Pharmaceutical Research*, (1995), vol. 12, No. 7, pp. 1055-1059.

Lee et al., "The sodium lauryl sulfate model: an overview", *Contact Dermatitis*, 33: 1-7, 1995.

Loser et al., "FK506 Controls CD40L-Induced Systemic Autoimmunity in Mice," *J. Invest. Derm.* (2006) 126:1307-1315.

Mancinelli et al., "The Pharmacokinetics and Metabolic Disposition of Tacrolimus: A Comparison Across Ethnic Groups," *Clinical Pharmacology & Therapeutics*, vol. 69, No. 1, pp. 24-31, 2001.

Martinet et al., "Evaluation of the In Vitro and In Vivo Effects of Cyclosporine on the Lung T-Lymphocyte Alveolitis of Active Pulmonary Sarcoidosis," *Am. Rev. Respir. Dis.*, (1998), 138:1242-1248.

McAlister et al., "Cost of Liver Transplantation Using Tacrolimus," *Transplantation Proceedings*, (1998), 30:1502.

McConville et al., "Targeted high lung concentrations of itraconazole using nebulized dispersions in a murine model," *Pharmaceutical Research* (2006) 23:901-911.

Mentzer et al., "Tacrolimus as a Rescue Immunosuppressant After Heart and Lung Transplant," *Transplantation*, Jan. 15, 1998, vol. 65, pp. 109-113.

Miller et al., "Lower Respiratory Tract Structure of Laboratory Animals and Humans: Dosimetry Implications," *Aerosol Science and Technology*, (1993), 18:3, pp. 257-271.

Moffati et al., "Potential for Improved Therapeutic Index of FK506 in Liposomal Formulation Demonstrated in a Mouse Cardiac Allograft Model," *Transplantation*, May 15, 1999, vol. 67, No. 9, pp. 1205-1208.

Mok et al., "Tacrolimus for Induction Therapy of Diffuse Proliferative Lupus Nephritis: An Open-Labeled Pilot Study," *The International Society of Nephrology*, (2005), pp. 813-817.

Morris-Stiff et al., "Pharmaco-Economic Study of FK 506 (Prograf) and Cyclosporine A Neoral in Cadaveric Renal Transplantation," *Transplantation Proceedings*, (1996), 30:1285-1286.

NEUSILUN® product brochure, Fuji Chemical Industry Co., Ltd., Jul. 2009.

Neylan et al., "Assessment of the Frequency and Costs of Post-transplantation Hospitalizations in Patients Receiving Tacrolimus Versus Cyclosporine," *American Journal of Kidney Diseases*, Nov. 1998, vol. 32, No. 5, pp. 770-777.

Office Communication issued in Canadian Patent Application No. 2,678,455, dated Nov. 30, 2015.

Office Communication issued in corresponding Canadian Patent Application No. 2,678,455, dated Dec. 28, 2016.

Office Communication issued in U.S. Appl. No. 14/621,337, mailed Oct. 26, 2018.

Office Communication issued in U.S. Appl. No. 15/385,369, mailed Sep. 20, 2017.

Overhoff et al., "Novel ultra-rapid freezing particle engineering process for enhancement of dissolution rates of poorly water-soluble drugs", *European Journal of Pharmaceutics and Biopharmaceutics*, 65(1): 57-67, 2007.

Overhoff et al., "Use of thin film freezing to enable drug delivery: a review", *J Drug Del Sci Tech.*, 19(2): 89-98, 2009.

Payne et al., "Phenotype-specific treatment of difficult asthma in children", *Pediatric Respiratory Reviews*, 5: 116-123, 2004.

Peters et al., "Tacrolimus: A Review of its Pharmacology, and Therapeutic Potential in Hepatic and Renal Transplantation," *Drugs*, (1993), 46(4):746-794.

Pilcer et al., "Formulation strategy and use of excipients in pulmonary drug delivery", *International Journal of Pharmaceutics*, 392: 1-19, 2010.

Pirsch et al., "A Comparison of Tacrolimus (FK506) and Cyclosporine for Immunosuppression After Cadaveric Renal Transplantation. FK506 kidney transplant study group," *Transplantation*, Apr. 15, 1997, vol. 63, pp. 977-983.

Plosker et al., "Tacrolimus: A Further Update of its Pharmacology and Therapeutic Use in the Management of Organ Transplantation," *Drugs*, Feb. 2000, 59(2):323-389.

Rogers et al., "A novel particle engineering technology to enhance dissolution of poorly water soluble drugs: spray-freezing into liquid," *Eur. J. Pharm. Biopharm.* (2002) 54:271-280.

Rogers et al., "A novel particle engineering technology: spray-freezing into liquid," *Int. J Pharm.*, (2002) 242:93-100.

Rogers et al., "Enhanced aqueous dissolution of a poorly water soluble drug by novel particle engineering technology: spray-freezing into liquid with atmospheric freeze-drying," *Pharm. Res.*, (2003) 20:485-493.

Rogers et al., "Micronized powders of a poorly water soluble drug produced by a spray-freezing into liquid-emulsion process," *Eur. J. Pharm. Biopharm.* (2003) 55:161-172.

Sengoku et al., "Effect of FK506 Eye Drops on Late and Delayed-Type Responses in Ocular Allergy Models," *Clin Exp Allergy*, (2003), 33:1555-1560.

Shoji et al., "Comparison of Topical FK506 Treatment for the Experimental Allergic Conjunctivitis Model in Balbi c Mice," *Jpn J. Opthithalmol*, (2005), vol. 49:205-210.

Sinswat, "Enhancing the Delivery of Poorly Water Soluble Drugs Using Particle Engineering Technologies," *Dissertation*, The University of Texas at Austin, Dec. 2006, 314 pages.

Starzl et al., "FK 506 for Liver, Kidney, and Pancreas Transplantation," *The Lancet*, Oct. 28, 1989, pp. 1000-1006.

Steckel et al., "The effect of formulation variables on the stability of nebulized aviscumine," Int. J. Pharm. (2003) 257:181-194.

Sun et al., "Preparation of activated carbon with large specific surface area from reed black liquor", *Environmental Technology* (abstract only), 28(5), 2007.

Tacca, "Prospects for personalized immunosuppression: pharmacologic tools—a review," *Transplant Proc.* (2004) 36:687-689.

Tamura et al., "The Site-Specific Transport and Metabolism of Tacrolimus in Rat Small Intestine," *J Pharmacol Exp Ther* (2003) 306:310-316.

Tanabe et al., "Calcineurin Inhibitors in Renal Transplantation—What is the Best Option?" *Drugs*, (2003), 63(15):1535-1548.

Taylor et al., "Ultrasonic Nebulisers for Pulmonary Drug Delivery," *International Journal of Pharmaceutics*, (1997), 153:93-104.

Tsuneroi et al., "[Study on antirejection effect of inhalation administration of FK506 in allogeneic rat lung transplantation model]", *Japanese Journal of Transplantation*, Congress extra edition, 39: 237, 2004.

Van Drooge et al., "Incorporation of lipophilic drugs in sugar glasses by lyophilization using a mixture of water and tertiary butyl alcohol as solvent," *J Pharm. Sci.* (2004) 93:713-725.

Vaughn et al., "Single dose and multiple dose studies of itraconazole nanoparticles", *Eur J Pharm Biopharm.*, 63: 95-102, 2006.

Venkataramanan et al., "Clinical Pharmacokinetics of Tacrolimus," *Clin. Pharmacokinet*, (1995), 29 (6):404-430.

Venkataramanan et al., "Pharmacokinetics of FK 506 Following Oral Administration: A Comparison of FK 506 and Cyclosporine," *Transplant Proc.*, Feb. 1991, 23:931-933.

Waldrep et al., "Experimental pulmonary delivery of cyclosporine a by liposome aerosol", *International Journal of Pharmaceutics*, 160: 239-249, 1998.

Waldrep, "New Aerosol Drug Delivery Systems for the Treatment of Immune-Mediated Pulmonary Diseases," *Drugs of Today*, (1998), 34(6):549-561.

Wierik et al., "Formulation of lactose for inhaled delivery systems," *Pharm. Tech. Eur.* (2002) 11 :1-5.

Woodruff et al., "Genome-wide profiling identifies epithelial cell genes associated with asthma and with treatment response to corticosteroids", *PNAS*, 104(40): 15858-15863, 2007.

(56) References Cited

OTHER PUBLICATIONS

Yamashita et al., "Establishment of new preparation method for solid dispersion formulation of tacrolimus", *International Journal of Pharmaceutics*, 267: 79-91, 2003.

Yang et al., "High bioavailability from nebulized itraconazole nanoparticle dispersions with biocompatible stabilizers", *Int J Pharmaceutics*, 361: 177-188, 2008.

Ying et al., "Cyclosporin A, apoptosis of BAL T-cells and expression of Bcl-2 in asthmatics", *Eur Respir J.*, 22: 207-212, 2003.

Yu et al., "Preparation and characterization of microparticles containing peptide produced by a novel process: spray freezing into liquid," *Eur. J. Pharm. Biopharm.* (2002) 54:221-228.

Zeng et al., "The controlled delivery of drugs to the lung", *International Journal of Pharmaceutics*, 124: 149-164, 1995.

\* cited by examiner

METHODS FOR MAKING COMPOSITIONS FOR PULMONARY ADMINISTRATION

CROSS-REFERENCE TO RELATED APPLICATIONS

This application is a continuation of U.S. application Ser. No. 16/294,885, filed Mar. 6, 2019, which is a continuation of U.S. application Ser. No. 14/621,337, now U.S. Pat. No. 10,231,955, filed Feb. 12, 2015, which is a continuation of U.S. application Ser. No. 12/522,774, now U.S. Pat. No. 9,044,391, filed Mar. 2, 2010, as a national phase application under 35 U.S.C. § 371 of International Application Serial No. PCT/US2008/050795, filed Jan. 10, 2008, which claims priority to U.S. Provisional Application Ser. No. 60/884,383, filed Jan. 10, 2007, the entire contents of each of which are incorporated herein by reference.

TECHNICAL FIELD OF THE INVENTION

The present invention relates in general to the field of pulmonary delivery, and more particularly, to novel compositions and methods for the manufacture of immunosuppressive drug compositions for pulmonary delivery.

BACKGROUND OF THE INVENTION

Without limiting the scope of the invention, its background is described in connection with pulmonary delivery.

The treatment of solid organ transplants, especially lung transplants, with the currently available immunosuppressive drugs is limited due to poor penetration into the lung following oral or intravenous administration, associated with significant adverse effects following long term treatment. Despite the development of oral formulations for each of these drugs, low and variable systemic bioavailability, significant side effects and a narrow therapeutic window has limited their use and effectiveness.

Pulmonary formulations of cyclosporine have been developed by dissolving cyclosporine in the solvents such as ethanol or propylene glycol. However, the results with these solvents were unsatisfactory due to the irritating properties of these solvents. Lidocaine anesthesia of airways was required prior to aerosol dosing. More importantly, nebulization was complicated due to the precipitation of cyclosporine within the nebulization chamber. Furthermore, cyclosporine is highly toxic and has not had a significant effect on increasing long-term transplant survival. Given the enhanced immunosuppressive activity of tacrolimus (10 to 100 times more potent than cyclosporine), it is clear that improvements in delivery of tacrolimus without using irritating solvents will lead to lower infection rates using prophylaxis treatment and lowered cost with more efficacious therapy.

SUMMARY OF THE INVENTION

The present invention relates to the improved pharmaceutical compositions that include rapidly dissolving nanoparticles of tacrolimus that are administered by pulmonary delivery. More particularly, the compositions made by fast freezing technology are suitable as a respirable nanoparticle with rapid dissolution rate, high surface area, high potency (50-75% potency) and able to overcome poor bioavailability of drugs. The compositions of the present invention are highly porous, amorphous and nanostructured particles with high drug dissolution rates and high surface area enabling effective treatment of organ rejection due to enhanced drug bioavailability. The compositions presented overcome poor and variable bioavailabilities of drugs effective for both local delivery and systemic delivery in the lung.

More particularly, the present invention includes compositions and methods for the pulmonary delivery of a rapid dissolving, high potency, substantially amorphous nanostructured aggregate of tacrolimus and a stabilizer matrix that includes, optionally, a polymeric or non-polymeric surfactant, a polymeric or non-polymeric saccharide or both, wherein the aggregate has a surface area greater than 5 $m^2/g$ as measured by BET analysis and exhibiting supersaturation for at least 0.5 hours when 11 to 15-times the aqueous crystalline solubility of tacrolimus is added to simulated lung fluid. The simulated lung fluid may include 100 mL of modified simulated lung fluid with 0.02% w/v L-α-phosphatidylcholine dipalmitoyl (DPPC) maintained at 37° C. and stirred with a paddle speed of 100 RPM in a small volume dissolution apparatus. The composition of the present invention will generally exhibit greater than about 80% drug dissolved in about 1 hour when an amount equivalent to about 0.59-times the aqueous crystalline solubility of tacrolimus is added to 100 mL of modified simulated lung fluid with 0.02% w/v DPPC maintained at 37° C. and stirred with a paddle speed of 50 RPM in a small volume dissolution apparatus.

For example, the supersaturation of tacrolimus may be for at least 1, 2, 3 or 4 hrs and the nanostructured aggregate may display a solubility greater than crystalline solubility in modified simulated lung fluid with 0.02% w/v DPPC maintained at 37° C. and stirred with a paddle speed of 100 RPM in a small volume dissolution apparatus. The aggregate will generally provide a lung deposition of greater than about 0.10 μg/g wet whole lung tissue weight when administered by nebulization to a mouse weighing between 16 g and 32 g using the pre-clinical rodent dosing apparatus. In one example, the nanostructured aggregate has a surface area of greater than about 5, 10, 20 or 30 $m^2/g$. The nanostructured aggregate may also be provided for immediate release, extended release, pulsed release, delayed release, controlled release and combinations thereof.

In one example, the composition may be formulated as a dispersion for nebulization that is prepared by admixing the nanostructured aggregate containing tacrolimus with an aqueous carrier and nebulized by a nebulizer, an air-jet nebulizer, an ultrasonic nebulizer or a micro-pump nebulizer. The respirable fraction of the nebulized droplets is generally greater than about 40, 50, 60, 70, or 80% as measured by a non-viable 8-stage cascade impactor at an air flow rate of 28.3 L/min. The composition may be suitably adapted for delivery using a metered dose delivery device a dry powder inhalation device or a pressurized metered dose inhalation device.

The substantially amorphous nanostructured aggregate may be made by one or more of the following methods: freezing spray, freezing into liquid, spray freezing into vapor, ultra-rapid freezing or spray drying. For example, the substantially amorphous nanostructured aggregate is made by solvent precipitation, antisolvent precipitation, continuous precipitation or evaporative precipitation into aqueous solution. In another method, the tacrolimus is dissolved in solvent or co-solvent mixture capable of dissolving all of the components of the composition together with a stabilizing pharmaceutical excipient, wherein a resultant dry powder having tacrolimus present in individual particles at from 5% to 99% by weight is produced upon spray freezing into liquid or ultra-rapid freezing, followed by lyophilization.

The tacrolimus may be combined with any stabilizing pharmaceutical excipient, e.g., a carbohydrate, organic salt, amino acid, peptide, or protein which produces a powder upon spray freezing into liquid or ultra-rapid freezing. Non-limiting examples of stabilizing pharmaceutical excipients include a carbohydrate selected from the group consisting of mannitol, raffinose, lactose, maltodextrin, trehalose and combinations thereof. The aggregate may include one or more highly wettable nanoparticle domains and/or nanostructured aggregates that quickly wet and dissolve in an aqueous solution.

The present invention also includes a method of making an pulmonary composition by mixing tacrolimus with a surfactant, a stabilizer, or a combination or a surfactant and stabilizer matrix and ultra-rapid freezing the tacrolimus and the surfactant/stabilizer matrix into a rapid dissolving high potency amorphous nanoparticle by spray freezing into liquid or ultra-rapid freezing, wherein the nanoparticle has a surface area greater than 5 $m^2/g$ as measured by BET analysis and exhibiting supersaturation for at least 0.5 hours when 15-times the aqueous crystalline solubility of tacrolimus is added to modified simulated lung fluid with 0.02% w/v DPPC. For example, the aggregate of the present invention displays a solubility of greater than about 2 times that of crystalline tacrolimus solubility. The pulmonary composition may be provided for immediate release, extended release, pulsed release, delayed release, controlled release and combinations thereof. The tacrolimus may be dissolved in a solvent together with a stabilizing pharmaceutical excipient, wherein a dry powder having tacrolimus present in individual particles at from 5% to 99% by weight is produced upon spray freezing into liquid or ultra-rapid freezing.

Yet another embodiment of the present invention is a high surface area nanoparticle that is an amorphous aggregate tacrolimus nanoparticle within a surfactant/stabilizer matrix adapted for pulmonary administration with a surface area greater than 5 $m^2/g$ as measured by BET analysis and exhibiting supersaturation for at least 0.5 hours when 15-times the aqueous crystalline solubility of tacrolimus is added to modified simulated lung fluid with 0.02% w/v DPPC.

Another embodiment of the present invention includes compositions and methods for reducing transplant rejection in a subject by mixing tacrolimus with a surfactant, a stabilizer matrix, or a combination or a surfactant and stabilizer matrix; and ultra-rapid freezing the tacrolimus and the surfactant/stabilizer matrix into a rapid dissolving high potency amorphous nanoparticle by spray freezing into liquid or ultra-rapid freezing to form a tacrolimus nanoparticle, wherein the tacrolimus nanoparticle comprises a surface area greater than 5 $m^2/g$ as measured by BET analysis and exhibiting supersaturation for at least 0.5 hours when 11 to 15-times the aqueous crystalline solubility of tacrolimus is added to modified simulated lung fluid; and treating the subject with an effective amount of the tacrolimus nanoparticle composition to prevent transplant rejection. In one aspect, the tacrolimus nanoparticle is adapted for pulmonary delivery. In another aspect, the tacrolimus nanoparticle is provided to prevent rejection of a lung transplant. In another aspect, the tacrolimus nanoparticle is provided at between 0.1 mg/ml to 100 mg/ml.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
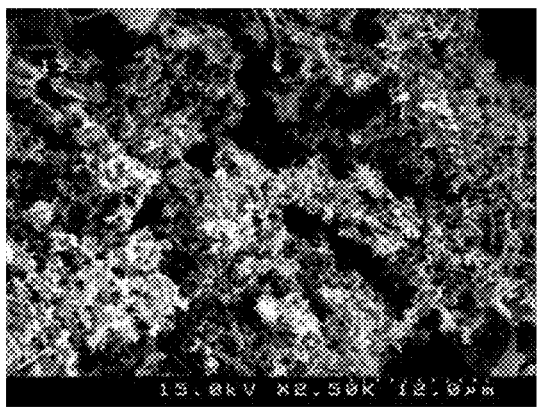
FIGS. 1A and 1B are SEM images of nanoparticles that include tacrolimus (TAC):Lactose (1:1) at two different magnifications.
Figure 1B:
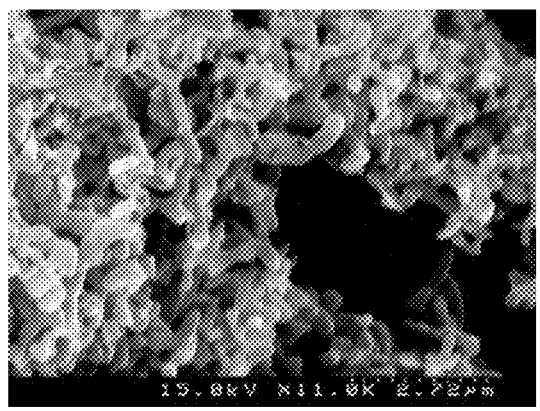
Figure 2A:
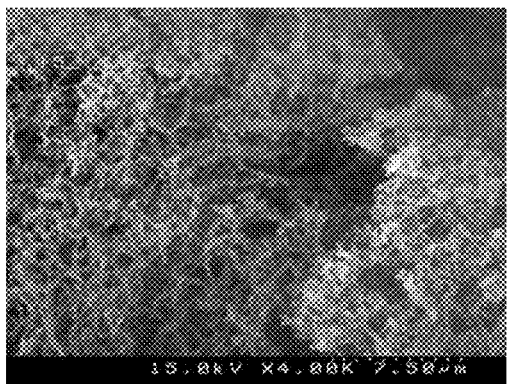
FIGS. 2A and 2B are SEM images of nanoparticles containing tacrolimus (TAC):Poloxamer 407 (4:1)
Figure 2B:
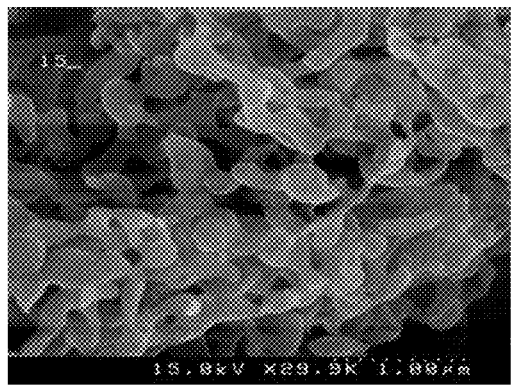

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "BET Analysis" refers to a method for measuring the surface area of the exposed surface of a solid sample on the molecular scale. The BET (Brunauer, Emmet, and Teller) theory is typically used to determine the area of solids. Commonly, samples are prepared by heating and simultaneously evacuating or flowing gas over the sample to remove the liberated impurities. The prepared samples are then cooled with liquid nitrogen and analyzed by measuring the volume of gas (typically $N_2$ or Kr) adsorbed at specific pressures. Krypton gas is often used when the measured surface is expected to be less than 2 $m^2/g$ (typically pharmaceutical samples and natural organic materials). The skilled artisan will recognize that several types of instruments may be used for measuring surface area, which depends upon the extent of the surface or the gas required to achieve the best results. Examples of equipment that may be used includes the ASAP 2020 and ASAP 2405 Kr, the Tristar 3000, the Gemini 2380, and the Flowsorb 2310.

As used herein, the term "modified simulated lung fluid with 0.02% w/v DPPC" refers to the composition reported in Table 1 of the reference Davies, N. M. and Feddah, M. R. (2003) A novel method for assessing dissolution of aerosol inhaler products. *International Journal of Pharmaceutics*, 255, 175-187. As seen in Table 1 of Davies, et al., the composition includes: calcium ion, magnesium ion, potassium ion, sodium ion, bicarbonate, chloride ion, citrate ion, acetate ion, phosphate ion, sulfate ion, and DPPC. The pH ranges between 7.3 and 7.4. The modified simulated lungs fluid as describe herein is composed of calcium, magnesium, potassium, sodium, bicarbonate, chloride, citrate, acetate, phosphate, and sulphate at 5, 2, 4, 145, 156, 31, 114, 1, 7, 2, and 1 mEq/L respectively. Additionally, 0.02% L-α-phosphatidylcholine was added according to the method described in Davies et al.

TABLE 1

Compositions of actual lung fluid, simulated lung fluids and the modified simulated lung fluid by DPPC (mEq./1).

| Ion | Actual[a] | Simulated lung fluid[b] | Modified simulated lung fluid with 0.02% DPPC |
|---|---|---|---|
| Calcium, $Ca^{2+}$ | 5.0 | 5.0 | 5.0 |
| Magnesium, $Mg^{2+}$ | 2.0 | 2.0 | 2.0 |
| Potassium, $K^+$ | 4.0 | 4.0 | 4.0 |
| Sodium, $Na^+$ | 145.0 | 145.0 | 145.0 |
| Total cations | 156.0 | 156.0 | 156.0 |
| Bicarbonate, $HCO_3^-$ | 31.0 | 31.0 | 31.0 |
| Chloride, $Cl^-$ | 114.0 | 114.0 | 114.0 |
| Citrate, $H_5C_6O_7^{3-}$ | — | 1.0 | 1.0 |
| Acetate, $H_3C_2O_2^-$ | 7.0 | 7.0 | 7.0 |

TABLE 1-continued

Compositions of actual lung fluid, simulated lung fluids and the modified simulated lung fluid by DPPC (mEq./1).

| Ion | Actual[a] | Simulated lung fluid[b] | Modified simulated lung fluid with 0.02% DPPC |
|---|---|---|---|
| Phosphate, $HPO_4^{2-}$ | 2.0 | 2.0 | 2.0 |
| Sulphate, $SO_4^{2-}$ | 1.0 | 1.0 | 1.0 |
| Protein | 1.0 | — | — |
| L-α-Phosphatidylcholine | — | — | $200_{mg}$ |
| Total anions | 156.0 | 156.0 | 156.0 |
| pH | 7.3-7.4 | 7.3-7.4 | 7.3-7.4 |

DPPC: L-α-phosphatidylcholine.
[a]Diem and Lenter (1970).
[b]Moss (1979).

As used herein, the term "exhibiting supersaturation" refers to a solution that contains more of the dissolved tacrolimus than could be dissolved by the modified simulated lung fluid with 0.02% w/v DPPC compared to the crystalline tacrolimus.

As used herein, the term "quickly wets" refers to the ability of the nanostructured aggregates to be wetted by the modified simulated lung fluid with 0.02% w/v DPPC or lung fluids in vivo at body temperature (37° C.).

As used herein, the term "wet whole lung tissue weight" refers to the total lung weight of a mouse.

As used herein, the term "pharmaceutical carrier" means the inactive components of the pharmaceutical composition.

As used herein, the term "surfactant" means a substance that reduces the surface tension of a liquid, thereby causing it to spread more readily on a solid surface. Examples of surfactants for use with the present invention, include, all surfactants suitable for administration to the lungs, including sodium salts of cholate, deoxycholate, glycocholte and other bile salts; Span 85, Lauryl-beta-D-maltoside, palmitic acid, glycerol trioleate, linoleic acid, DPPC oleyl alcohol, oleic acid, sodium oleate, and ethyl oleate.

As used herein, the term "pre-clinical rodent dosing apparatus" refers to the apparatus reported by J. T. McConville, P. Sinswat, J. Tam, K. P. Johnston and R. O. Williams III, In vitro and in vivo validation of a high-concentration pre-clinical rodent dosing apparatus for inhalation, Proceedings of the American Association of Pharmaceutical Scientists, San Antonio, TX, October, 2006, relevant portions incorporated herein by reference. An animal dosing chamber was designed which consisted of hollow tubing (20×4.5 cm; nominal wall thickness of 0.4 cm) with four 1.75 cm adapter holes drilled at 7 cm intervals (2 holes along each side). The adapter holes were constructed to accept rodent restraint tubes from the Battelle® toxicology testing unit. A standard itraconazole (ITZ) colloidal suspension was nebulized into the apparatus for 5 minutes using a micro-pump nebulizer. Atomized droplets containing ITZ were driven into the chamber at a flow rate of 1 L/min. ITZ concentrations were measured in vitro at the 4 adapter ports, and in vivo from the lungs of 8 outbred-ICR mice in the appropriate mice restraining tubes at the adapter ports.

The technology makes use of existing excipients used are all selected from the GRAS list approved by the FDA, their use is approved by the FDA, or they are naturally occurring in mammalian tissues. They are used frequently in oral tablet or parenteral preparations and indicate minimal toxicity levels. These are used in conjunction with the active ingredient to form a stable nanosized dosage form.

It is important that processed drug product contains stabilized nanoparticles with high surface area to obtain high dissolution rates. Other processing technologies can be used such as fast freezing, antisolvent and precipitation methods.

It was also found that TAC has the ability to reverse ongoing rejection. Subsequently, numerous studies have confirmed the effectiveness of TAC as primary therapy in a variety of solid organ transplants. Of importance, the enhanced immunosuppressive activity of TAC is achieved without increased risk of infection or malignancy. Although many studies revealed that TAC may have superior immunosuppressive activities compared to cyclosporine, erratic absorption from the gastrointestinal tract following oral administration have limited the drug's clinical potential.

The average oral bioavailability of this drug is approximately 25% in adult patients. High cost of rejection therapy associated with tacrolimus is about $34,200 in the first year. The compositions of the present invention composed of porous aggregates of small particles with high drug dissolution rates and high surface area enabling effective treatment of organ rejection due to enhanced drug bioavailability.

TABLE 2

Surface Area Analysis

| Formulations | Specific Surface Area [$m^2/g$] |
|---|---|
| TAC Bulk Powders | 0.533 |
| TAC:Lactose (1:1) | 44.28 |
| TAC:Poloxamer 407 (4:1) | 40.07 |

Particle Morphology. SEM—The powder samples were sputter coated with gold-palladium for 35 seconds and viewed using a Hitachi S-4500 field emission scanning electron microscope. SEM indicates the presence of porous aggregated small particles X-Ray Diffraction. The x-ray diffraction pattern of powders were analyzed using a Philips 1710 x-ray diffractometer with a copper target and nickel filter (Philips Electronic Instruments, Inc., Mahwah, NJ). The leveled powder was measured from 10 to 40 2-theta degrees using a step size of 0.05 2-theta degrees and a dwell time of one second. No corresponding tacrolimus peaks can be identified.

Figure 5:
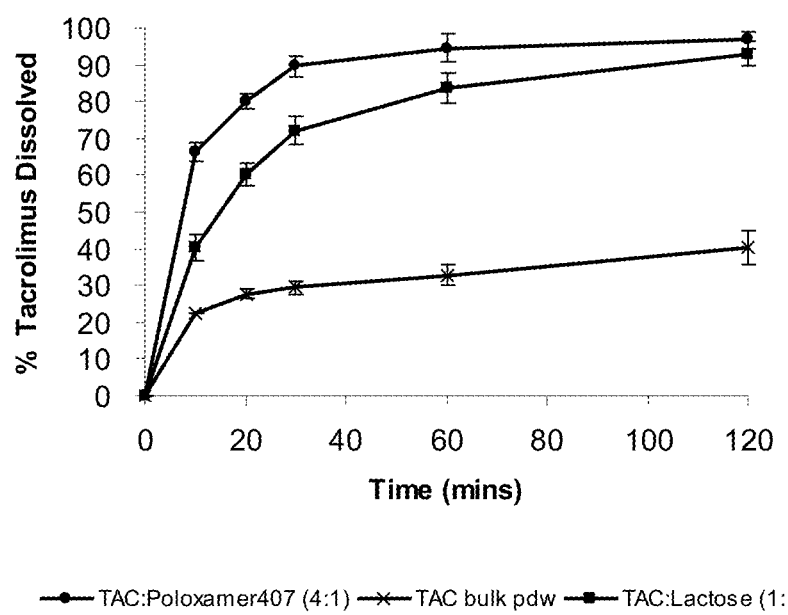
FIG. 5 is a graph that shows dissolution testing results. Dissolution testing was conducted at sink conditions using a USP Type 2 apparatus (VanKel VK6010 Dissolution Tester with a Vanderkamp VK650A heater/circulator); dissolution media was 900 mL of modified simulated lung fluid containing 0.02% DPPC maintained at 37° C. and stirred at 100 rpm; dissolution profiles were determined in replicates of 6.

Dissolution of oral formulations (n=6). Dissolution testing was performed on the powder samples using USP Type 2 apparatus (VanKel VK6010 Dissolution Tester with a Vanderkamp VK650A heater/circulator). An equivalent of 4 mg tacrolimus was added to 900 ml of modified simulated lung fluid with 0.02% DPPC dissolution media and stirred at 100 rpm. The dissolution media was maintained at 37.0±0.2° C. Five milliliter samples were withdrawn at 10, 20, 30, 60 and 120 minute time points, filtered using a 0.45 μm GHP Acrodisc filter and analyzed using a Shimadzu LC-10 liquid chromatograph (Shimadzu Corporation, Kyoto, Japan). A 70:30 acetonitrile:water mobile phase at 1 ml/min eluted the TAC peak at 6 minutes. For the formulations prepared for FIG. 5, the tacrolimus absorbance was measured at λ=220 nm.

TABLE 3

Anderson Cascade Impactor - Aeroneb ® Professional Micropump Nebulizer data.

| Formulations | Total Emitted Dose [μg/min] | Respirable fraction [%] | MMAD(GSD) [μm] |
|---|---|---|---|
| TAC:Lactose (1:1) | 5082 | 74.6 | 2.57(2.24) |
| TAC:Poloxamer 407 (4:1) | 4917 | 71.1 | 2.75(1.86) |

MMAD = Mass Median Aerodynamic Diameter
GSD = Geometric Standard Deviation

Good aerosolization performance was achieved. Greater than 70% respirable fractions are indicated for all formulations using the Aeroneb® Professional nebulizer. Mass median aerodynamic diameters between 1 and 5 μm are also indicated for all formulations, using this nebulizer.

This study were to produce nanostructured aggregates of tacrolimus (TAC) intended for pulmonary delivery using ultra-rapid freezing (URF), and to investigate the physicochemical and pharmacokinetic characteristics of the nanostructured aggregates containing amorphous or crystalline nanoparticles of TAC. Two URF formulations were investigated for pulmonary delivery, and compared to bulk unprocessed TAC, these were: TAC and lactose (1:1 ratio; URF-TAC:LAC) and TAC alone (URF-TAC). TAC and water soluble excipient i.e. lactose were dissolved in acetonitrile and water, respectively. Two solutions were mixed to obtain 60:40 ratio of the resulting organic/aqueous co-solvent system which was then frozen on the cryogenic substrate. The cosolvent was then frozen on the URF cryogenic substrate and the frozen compositions were collected and lyophilized to form the dry powder for nebulization. In vitro results revealed similar physiochemical properties for both URF formulations. BET analysis showed high surface areas of 29.3 $m^2/g$ and 25.9 $m^2/g$ for the URF-TAC:LAC and URF-TAC, respectively, and 0.53 $m^2/g$ for the unprocessed TAC, respectively. Scanning electron microscopy (SEM) showed nanostructured aggregates containing nanoparticles of TAC. The dissolution of TAC was 83.6% at 1 hr for the URF-TAC:LAC, compared to 80.5% for the URF-TAC and 30% dissolved for the unprocessed TAC, respectively. Similar aerodynamic particle sizes of 2-3 μm, and fine particle fraction between 70-75% for the URF-TAC:LAC and URF-TAC were determined by cascade impactor data. X-ray diffraction (XRD) results indicated that URF-TAC was crystalline, whereas URF-TAC:LAC was amorphous. The supersaturated dissolution profiles were in agreement with these results. URF-TAC:LAC displayed the ability to supersaturate in the dissolution media to about 11-times crystalline equilibrium solubility. In vivo studies were conducted in mice by dispersing the URF formulations in deionized water and nebulizing the dispersed URF formulations using a specially designed nose-only dosing apparatus. The pharmacokinetic profiles obtained showed comparable $AUC_{(0-24)}$, higher $C_{max}$, and lower $T_{max}$ for the URF-TAC:LAC compared to the URF-TAC. Therefore, rapidly dissolving, pulmonary formulations containing nanostructured aggregates of amorphous or crystalline TAC were developed using the URF technology. The URF processed formulations were demonstrated to be effectively delivered as an aqueous dispersion of TAC nanoparticle via nebulization, with a similar in vivo performance by displaying the comparable extent of drug absorption.

Tacrolimus (TAC) is a widely used immunosuppressive agent isolated from *Streptomyces tsukubaensis*. It has proven to be a potent immunosuppressant in transplantation medicine for treatment of organ rejection and different immunological diseases such as pulmonary fibrosis and bronchiolar asthma [1-3]. TAC was first introduced as rescue therapy when cyclosporin A (CsA) therapy failed to prevent graft rejection. It has a mechanism of action similar to that of CsA, but its immunosuppressive activity is 10- to 100-times more potent than CsA [4,5]. TAC is currently available in both an intravenous and oral dosage form (commercially known as Prograf®). However, these current available dosage forms of the drug are poorly tolerated and provide a variable and/or low bioavailability [6]. The oral formulations of TAC present a considerable challenge as the drugs are practically insoluble in water and extensively metabolized from both CYP3A4 metabolism and p-glycoprotein efflux transport within the intestinal epithelium [7]. The oral bioavailability of TAC varies from 4% to 93% [8]. Inefficient or erratic drug absorption is primarily the result of incomplete absorption from the gastrointestinal tract and first-pass metabolism, which is subject to considerable inter-individual variation [8].

This invention focuses on a pulmonary drug delivery system based on, nanoparticles of TAC in order to overcome the above mentioned problems to improve bioavailability. The appealing aspects of inhaled drug nanoparticles include: Rapid dissolution of nanoparticles in the lung and the avoidance of hepatic first pass metabolism (which is especially useful for a drug that undergoes extensive metabolism in liver) [9,11]. Additionally, inhaled nanoparticles can increase local drug concentrations in the lung for potential therapeutic use in lung transplantation and pulmonary diseases. The treatment of lung transplant recipients is often limited due to poor penetration of drug into the lung following oral or intravenous administration [12]. Aerosolized drug will have direct access to the graft in lung transplant offering the possibility of much higher drug levels [13]. However, a major disadvantage of pulmonary delivery for drugs like TAC is limitations in the levels and types of excipients that are considered safe to use in pulmonary formulations. Although many surfactants or polymers such as cyclodextrins, poloxamers, polyethylene glycols (PEG) and glycerol have been studied in pulmonary formulations to aid drug solubilization in many research studies [14-16], these excipients have not been approved yet for commercial use by the FDA because of potential toxicity in the lung. Several clinical studies have demonstrated effective pulmonary delivery of CsA solutions in ethanol or propylene glycol prior to aerosolization in lung transplantation models [17-19]. However, the solvents have produced the results have shown unsatisfactory due to the irritating properties of these solvents to the airways. In addition, the use of high levels of ethanol or propylene glycol in formulations intended for pulmonary delivery have yet to be widely studied in humans. Recently, liposome technology has been investigated as a non-irritating alternative for pulmonary delivery of CsA, but the formulation had low drug loading and thus requires a lengthy nebulization period [20].

Pulmonary formulations containing TAC manufactured by ultra-rapid freezing (URF), without the inclusion of surfactants or polymeric excipients, were investigated. URF technology is a continuous, scalable cryogenic process produces nanostructured aggregates with high surface area resulting in high enhanced drug dissolution rates. Previously, spray freezing into liquid (SFL) was reported [21-26]. The rapid freezing rates achieved with the SFL process led to the production of amorphous nanostructured aggregates composed of primary particles, ranging from 100 to 200 nm, with high surface areas, high wettability and significantly enhanced dissolution rates. The URF process yields particles with similar properties as those produced by SFL. In URF a solution of the active and excipient in a suitable organic solvent or aqueous co-solvent is applied to the surface of a cryogenic solid substrate. The spray is frozen instantaneously, in 50 ms to 1 s, onto the surface of cryogenic solid substrate in a continuous manner [27,28]. URF powders exhibit desirable properties for enhancing bioavailability such as high surface area, increased drug dissolution rates, and amorphous character.

Nanostructured aggregates composed of amorphous or crystalline primary nanoparticles of TAC produced by the URF process are suitable for pulmonary delivery by nebulization, resulting in high lung and blood concentrations. The hypothesis is that high surface area and rapid dissolution rate obtained from nanostructured aggregates of TAC promote high systemic drug absorption via the lung, whilst still maintaining a desirable pulmonary residence time for potential local therapy. Relevant physicochemical properties (e.g. surface area, dissolution, crystallinity) of TAC nanostructured aggregates were characterized in order to understand how they influence in vivo drug absorption following single-dose nebulization of the particle dispersions. TAC was kindly provided by The Dow Chemical Company (Midland, MI). Lactose, magnesium chloride hexahydrate, sodium chloride, potassium chloride, sodium phosphate dibasic anhydrous, sodium sulphate anhydrous, calcium chloride dihydrate, sodium acetate trihydrate, sodium bicarbonate and sodium citrate dihydrate were analytical grade and purchased from Spectrum Chemicals (Gardena, CA). Dipalmitoylphosphatidylcholine (DPPC) was purchased from Sigma-Aldrich Chemicals (Milwaukee, WI). High performance liquid chromatography (HPLC) grade acetonitrile (ACN) was purchased from EM Industries, Inc. (Gibbstown, NJ). Liquid nitrogen was obtained from Boc Gases (Murray Hill, NJ). Deionized water was prepared by a Milli-Q purification system from Millipore (Molsheim, France).

Exemplary preparation of URF Formulations. TAC formulations were processed using URF. Two URF formulations considered for pulmonary delivery were TAC:lactose in a 1:1 ratio (URF-TAC:LAC) and TAC alone (URF-TAC). The compositions were prepared by dissolving TAC and hydrophilic excipient (if any) at a 1:1 ratio and 0.75% solids in a 60/40 mixture of acetonitrile and water. The solution of drug was applied to the surface of solid substrate, which is cooled using a cryogenic substrate maintained at −50° C. The frozen compositions were then collected and the solvent was removed by lyophilization using VirTis Advantage Tray Lyophilizer (VirTis Company Inc., Gardiner, NY). The lyophilization recipes used in this study is outlined in Appendix A. The dried powders were stored at room temperature under vacuum.

In Vitro Characterization of Powders for Pulmonary. X-ray Powder Diffraction (XRD). The XRD patterns of the powders were analyzed using a Philips 1710 x-ray diffractometer with a copper target and nickel filter (Philips Electronic Instruments, Inc., Mahwah, NJ). Each sample was measured from 5 to 45 2θ degrees using a step size of 0.05 2θ degrees and a dwell time of one second.

BET Specific Surface Area Analysis. Specific surface area was measured using a Nova 2000 v. 6.11 instrument (Quantachrome Instruments, Boynton Beach, FL). A known weight of powder was added to a 12 mm Quantachrome bulb sample cell and degassed for a minimum of three hours. The data recorded were then analyzed according to BET theory using NOVA Enhanced Data Reduction Software v. 2.13.

Scanning Electron Microscopy (SEM). A Hitachi S-4500 field emission scanning electron microscope (Hitachi High-Technologies Corp., Tokyo, Japan) was used to obtain SEM micrographs of the powder samples. Samples were mounted on conductive tape and sputter coated using a model K575 sputter coater (Emitech Products, Inc., Houston, TX, USA) with gold/palladium for 30 s. An accelerating voltage of 5-15 kV was used to view the images.

Dissolution Testing at Below Equilibrium Solubility. Dissolution testing at below equilibrium solubility was performed on the URF powder samples using a United States Pharmacopeia (USP) 27 Type 2 dissolution apparatus (Van-Kel VK6010 Dissolution Tester with a Vanderkamp VK650A heater/circulator, Varian, Inc. Palo Alto, CA). Powder samples (0.4 mg of TAC) equivalent to approximately 59% of the equilibrium solubility (6.8 µg/mL) were added to 100 mL of modified simulated lung fluids (SLF) with 0.02% DPPC as dissolution media [29]. The dissolution media was maintained at 37.0±0.2° C. and stirred at a constant rate of 50 rpm. Samples (1 mL) were withdrawn at 10, 20, 30, 60 and 120 minute time points, filtered using a 0.45 µm GHP Acrodisc filter (VWR, Inc., West Chester, PA) and analyzed using a Shimadzu LC-10 liquid chromatograph (Shimadzu Corporation, Kyoto, Japan) equipped with an Alltech ODS-2, 5 µm $C_{18}$ column (Alltech Associates, Inc., Deerfield, IL). The mobile phase consisted of a 70:30 (v/v) ACN: Water mixture, used at a flow rate of 1 mL/min. The maximum absorbance was measured at wavelength $\lambda_{max}$=214 nm.

Dissolution Behavior in the Formation of Supersaturated Solutions. Supersaturated dissolution profiles were generated according to the method previously described except using the small volume dissolution apparatus equipped with a paddle stirring mechanism. Each drug formulation was weighed out which corresponded to approximately 15-times the aqueous crystalline solubility of TAC in 100 mL of the modified simulated lung fluid with 0.02% DPPC. Paddle speed and bath temperature were maintained at 100 rpm and 37° C., respectively. An aliquot (1 mL) were removed from the small volume dissolution vessel at 10, 20, 30 and 60 minutes, then at 2, 4 and 24 hours. Each aliquot was filtered through a 0.2 µm nylon filter, and a 0.5 mL aliquot of each filtered solution was immediately mixed with 1 mL of acetonitrile (to ensure no re-crystallization of drug previously dissolved at 37° C.). The samples were analyzed for TAC concentration using the same HPLC procedure described previously. All studies were performed in triplicate.

In Vitro Aerosol Performance. The in vitro deposition characteristics of the dispersed and nebulized TAC formulations were investigated using a non-viable 8-stage cascade impactor (Thermo-Electron Corp., Symrna, GA, USA). The aerosolization behavior was described in terms of total emitted dose (TED), fine particle fractions (FPFs), mass median aerodynamic diameters (MMAD) and geometric standard deviation (GSD). The cascade impactor was assembled and operated in accordance with USP method 601 to assess the drug delivered. The powders were dispersed in water (10 mg/mL) and nebulized using an Aeroneb® Professional micropump nebulizer (Nektar Inc., San Carlos, CA) for 10 minutes at an air flow rate of 28.3 L/min. The flow rate was maintained by a vacuum pump (Emerson Electric Co., St. Louis, MO, USA) and calibrated by a TSI mass flow meter (Model 4000, TSI Inc., St. Paul, MN, USA). The mass deposited on each of the stages was collected and analyzed by HPLC as described herein. Each study was repeated in triplicate.

In Vivo Mouse Studies. Pulmonary Administration of URF Formulations. Pulmonary dosing of URF formulations was performed in healthy male ICR mice (Harlan Sprague Dawley, Inc., Indianapolis, IN). The study protocol was approved by the Institutional Animal Care and Use Committee (IACUCs) at the University of Texas at Austin, and all animals were maintained in accordance with the American Association for Accreditation of Laboratory Animal Care. Mice were acclimated and pre-conditioned in the restraint tube (Battelle, Inc., Columbus, OH) for 10-15 min./day for at least 2 days prior to dosing. Proper pre-conditioning is essential for reducing stress to mice, and maintaining a uniform respiration rate for the animals. A small animal dosing apparatus for inhalation was used to dose the mice for this study. The dosing apparatus includes a small volume hollow tube with dimensions of 20×4.5 cm (nominal wall thickness of 0.4 cm) with four 1.75 cm adapter holes drilled at 7 cm intervals (2 holes along each side). The adapter holes were constructed to accept rodent restraint tubes from the Battelle toxicology testing unit.

The URF processed powders were re-dispersed in water (10 mg/mL) followed by sonication for 1 min. prior to dosing. Nebulization of 3 mL of dispersions was conducted using an Aeroneb Professional micropump nebulizer for 10 min. dosing period. After pulmonary dosing, the mice were removed from the dosing apparatus and rested for 15 min. Two mice were sacrificed at each time point by $CO_2$ narcosis (0.5, 1, 2, 3, 6, 12, 24 and 48 hours). Whole blood (1-mL aliquots) was obtained via cardiac puncture and analyzed according to the standard ELISA procedure outlined hereinbelow. In addition, necropsy was performed on each mouse to extract lung tissue. Samples were stored at −20 C until assayed. TAC concentrations in lung tissue were determined using a previously HPLC assay as described below.

Enzyme-Linked Immunosorbent Assay (ELISA) for Analysis of TAC Concentrations in Blood. The determination of TAC in whole blood was performed using the PRO-Trac™ II FK 506 ELISA assay kit (Diasorin Inc., Stillwater, USA) in accordance with the manufacturer's instructions. Specifically, 50 μL of whole blood sample or standards were placed into a conical 1.5 mL polypropylene tube. Digestion reagent was freshly reconstituted, and 300 μL was added to all tubes. The tubes were vortexed for 30 seconds and incubated at room temperature for 15 min. These tubes was then placed on an aluminum heating block circulated with 75° C. water bath for 15 min to stop proteolysis. After vortexing, the tubes were centrifuged at room temperature at 1,800×g for 10 min. The supernatant (100 μL) was transferred to microtiter plate wells in duplicate from each centrifuged tube. Capture monoclonal anti-FK506 (50 μL) was added to the each well, and the plate was shaken at room temperature at 700 rpm for 30 min. TAC horseradish peroxidase conjugate (50 μL) was then added to each well, and the plate was shaken at room temperature at 700 rpm for an additional 60 min. The plate was washed, before the addition of 200 μL chromogen. The plate was then shaken at 700 rpm for a further 15 min at room temperature. The subsequent reaction in each plate well was terminated by the addition of 100 μL of stop solution. The absorbance in each well was read at the dual wavelengths of 450 and 630 nm. Data was plotted according to a four-parameter logistic (4PL) curve-fitting program.

Solid Phase Extraction and Drug Analysis of Lung Tissues using HPLC. Lung extraction was carried out using solid phase extraction to obtain TAC levels using reverse phase HPLC. The total lung weight was recorded individually from each mouse. Lung tissues were homogenized using a Polytron rotor-stator homogenizer (VWR Scientific Corporation, West Chester, PA) for 40 seconds in 1 mL of normal saline. The homogenized lung samples were then mixed with 0.5 mL solution of 0.4 N zinc sulfate heptahydrate in the mixture of methanol/water (70:30) solution and vortex mixed for 30 seconds. Acetonitrile (1 mL) was added to the homogenized samples before a further vortex mixing for 1.5 minutes, followed by centrifugation at 3000 rpm for 15 minutes to obtain a clear supernatant. Next, the supernatant was collected into a clean vial containing 1 mL purified water. Meanwhile C18 cartridges for solid phase extraction (Supelco Inc., Bellefonte, PA) were preconditioned. First, these columns were pretreated with 2 mL of acetonitrile, followed by 1 mL methanol and then washed with 1 mL of water before loading the supernatant through the column. The sample was transferred and drawn slowly through the column by reducing the vacuum. The column was washed again by passing 1.5 mL mixture of methanol/water (70:30) solution, followed by 0.5 mL of n-hexane and allowed it to dry under vacuum. The sample was finally eluted with 2 mL of acetonitrile (0.5 mL×4). The eluted material was evaporated under a dry nitrogen stream and then reconstituted with 250 µL of mobile phase using the previously described HPLC assay (below). Data was expressed as µg TAC/gram wet lung tissue analyzed.

Pharmacokinetics and Statistical Analysis. The lung tissue concentration vs. time was investigated using a non-compartmental model, while the whole blood concentration vs. time was evaluated using one-compartmental analysis from extravascular administration (via the lung compartment). Pharmacokinetic parameters were calculated using WinNonlin version 4.1 (Pharsight Corporation, Mountain View, CA). The pharmacokinetic profile of TAC was characterized by maximum concentration ($C_{max}$), time to $C_{max}$ ($T_{max}$), half-life ($T_{1/2}$) and area-under-the-curve (AUC) between 0-24 hours. AUC was calculated using the trapezoidal rule; $C_{max}$ and $T_{max}$ were determined from the concentration-time profiles; $T_{1/2}$ was calculated by using the elimination rate constant ($K_{el}$); $K_{el}$ was obtained from the ln concentration-time profiles.

Figure 4:
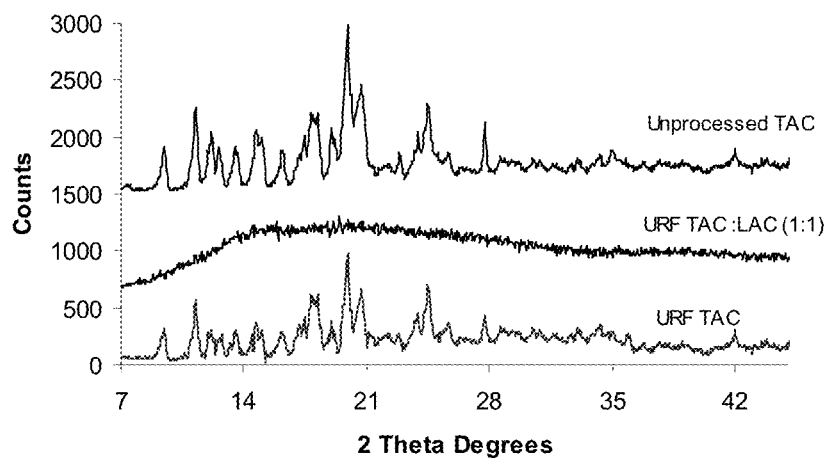
FIG. 4 shows the X-ray diffraction profiles of TAC URF formulations compared to unprocessed TAC.

In vitro characterization of URF formulations. The physicochemical properties of TAC powders produced by URF were investigated and compared to the unprocessed TAC. The XRD patterns of the URF formulations and unprocessed TAC are shown in FIG. 4. The diffractogram of URF-TAC was similar to that of unprocessed TAC, indicating a high degree of crystallinity. However, the XRD pattern of URF-TAC:LAC confirmed that this composition was amorphous. This suggests that lactose inhibited crystallization of TAC. It is well known that sugars such as lactose can be used to stabilize amorphous drugs, peptides and proteins during drying and subsequent storage [30,31]. The addition of sugars has been shown to extend the shelf life of amorphous systems by preventing crystallization. In addition, lactose is generally regarded as safe (GRAS) for use as an excipient in inhalation systems [32]. This is due to its non-toxic and degradable properties after administration [33].

Figure 3:
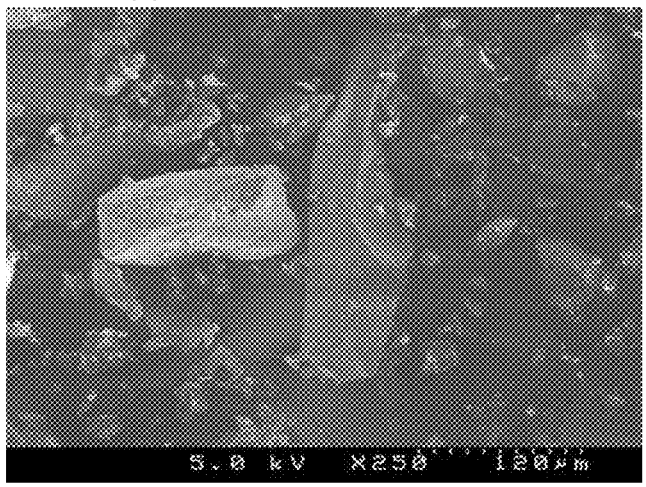
FIG. 3 is an SEM of TAC Crystalline Bulk Powders.

SEM micrographs of the two URF processed formulations are shown in FIGS. 1A-3 reveal distinct differences in morphology. The morphology of URF-TAC:LAC (FIGS. 1A-1B) showed highly porous, nanostructured aggregates. The micrograph at high magnification in FIG. 1B revealed that the aggregates were composed of branched interconnected nanorods with a diameter of approximately 100-200 nm. URF-TAC (FIGS. 2A-2B) appeared as more dense aggregates composed of submicron primary particles. In contrast, the SEM micrograph of unprocessed TAC indicated an irregular, dense and large crystal plate measuring between 50-100 µm in size (FIG. 3). Accordingly, the surface areas obtained by the URF processed formulations (URF-TAC:LAC and URF-TAC was 25.9 and 29.3 m$^2$/g, respectively) were significantly higher than ($p<0.05$) that of the unprocessed drug (0.53 m$^2$/g). This result is corroborated by the porous nanostructured aggregates of the URF powders observed by SEM.

The in vitro aerosol performance measured by cascade impaction for aqueous dispersions prepared from the URF processed powders are presented in Table 4.

TABLE 4

Physicochemical properties of TAC powder compositions prepared by the URF process and aerosol characteristics of aqueous dispersions of URF powder compositions delivery by nebulization.

| Formulations | Physical State of Drug | Surface Area (m$^2$/g) | TED (µg/min) | % FPF | MMAD (µm) | GSD |
|---|---|---|---|---|---|---|
| URF-TAC:LAC | Amorphous | 29.3 | 5082 | 74.6 | 2.57 | 2.24 |
| URF-TAC | Crystalline | 25.9 | 4823 | 70.2 | 2.86 | 1.97 |

TED: total emitted dose.
MMAD: mass median aerodynamic diameters.
GSD: geometric standard deviation.
FPF: fine particle fraction, as percentage of total loaded dose <4.7 µm.

Comparison of the data suggests similar aerodynamic properties of the drug particles aerosolized from the two URF formulations. The MMAD was 2.86 and 2.57 µm for URF-TAC:LAC and URF-TAC, respectively, and the GSD was less than 2.2 (Table 3). It can be concluded that the aerosol droplets contain aggregates of nanoparticles that are in the respirable range by nebulization. Aerodynamic particle size is the most important parameter in determining drug deposition in the lungs and must be considered when developing formulations for pulmonary delivery [34]. Aerosolized particles or droplets with a MMAD ranging from 1 to 5 µm are suitable for deep lung deposition, at the site of the alveoli, where maximum absorption may take place [35]. The optimal aerosolization properties of both URF formulations are also reflected in the high % FPF ranging from 70% to 75%, illustrating efficient lung delivery of drug particles. The TED was only slightly higher for URF-TAC:LAC (5082 µg/min) compared to that of URF-TAC (4823 µg/min). These values were not significantly different ($p>0.05$).

Figure 6:
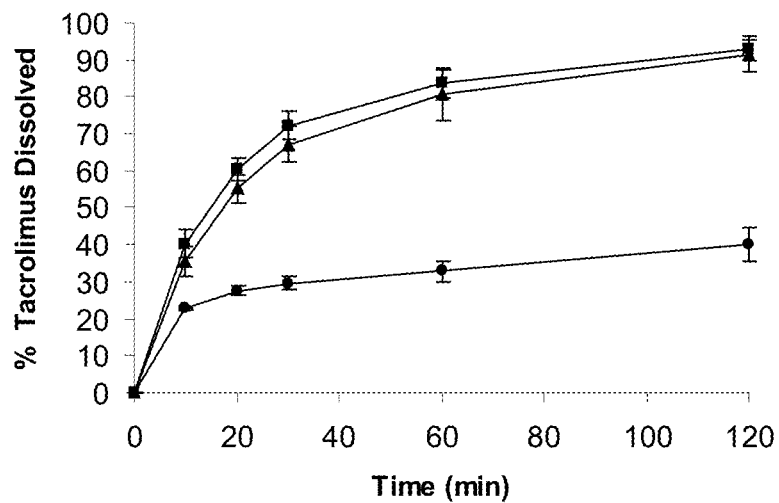
FIG. 6 is a graph that shows the sink dissolution profiles for (■) Amorphous URF composition TAC:lactose (1:1), (▲) Crystalline URF composition TAC alone and (●) Unprocessed crystalline TAC. The dissolution media was modified simulated lung fluid containing 0.02% DPPC at 100 rpm and 37° C. (equilibrium solubility of TAC in this media~6.8 μg/mL). Dissolution profiles were determined in replicates of 3.

The in vitro dissolution profiles of TAC in SLF media under sink conditions are shown in FIG. 6. The dissolution rates for both URF processed powders were significantly increased (p<0.05) as compared to the unprocessed TAC. Nanostructured aggregates of the URF processed powders were able to wet and dissolve quickly upon contact in SLF containing 0.02% DPPC, although the formulations contained no surfactant. For URF-TAC:LAC (i.e., amorphous, nanostructured aggregates), the dissolution of TAC was 72% in 30 minutes, compared to 67% for the URF-TAC (i.e., crystalline nanostructured aggregates) and 30% for the unprocessed TAC, respectively. The enhancement is most likely attributed to the high porosity and enhanced surface area of URF processed powders.

Figure 7:
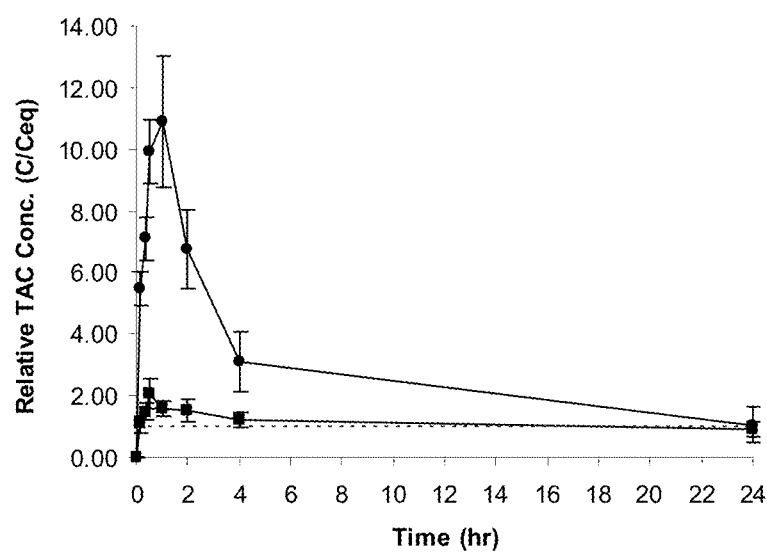
FIG. 7 is a graph that shows the supersaturated dissolution profiles for (□) Amorphous URF composition TAC:lactose (1:1); (■) Crystalline URF composition TAC alone and ( - - - ) Equilibrium solubility of TAC in the dissolution media (6.8 μg/mL). The dissolution media was modified simulated lung fluids (SLF) containing 0.02% DPPC at 100 rpm and 37° C. Dissolution profiles were determined in replicates of 3; C is measured concentration of TAC at a given time point and Ceq is equilibrium concentration of TAC.

Dissolution of TAC at supersaturated conditions was also conducted in the same media. Supersaturated dissolution profiles of the URF processed formulations containing 15-times the equilibrium solubility of TAC are compared in FIG. 7. The concentration obtained for the URF-TAC:LAC exceeded the equilibrium solubility of TAC, corresponding to a high degree of supersaturation in the SLF containing DPPC without the presence of surfactants or polymers in the formulation. The level of supersaturation corresponded to about 11-times the equilibrium solubility. This was due to the high-energy phase of the amorphous TAC particles. The maximum concentration occurred at 1 hour, and then decreased to about 3-times equilibrium solubility over the next 4 hours. A supersaturation dissolution profile was not observed for URF-TAC because of its crystalline nature.

Figure 8:
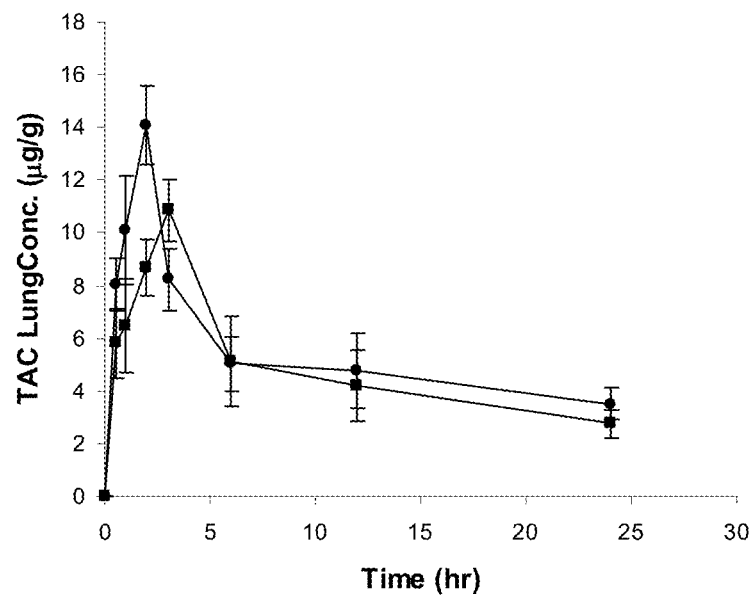
FIG. 8 is a graph that shows a comparison of mean lung concentration (μg TAC/g tissue) versus time profiles in mice of the URF formulations. (□) Amorphous URF composition TAC:lactose (1:1) and (■) Crystalline URF composition TAC alone.

In Vivo Pulmonary Studies. The pharmacokinetic absorption studies were conducted in mice. The murine model has been very effective for small scale inhalation studies [36]. The lung tissue concentration-time profiles following a single inhalation dose are shown in FIG. 8 while the corresponding pharmacokinetic parameters summarized in Table 5.

TABLE 5

In vivo pharmacokinetic parameters for the lung tissue concentrations of the URF formulations.

| Formulations | $C_{max}$ (µg/g) | $T_{max}$ (hrs) | $K_{el}$ (hrs$^{-1}$) | $T_{1/2}$ (hrs) | $AUC_{(0-24)}$ (µg · hr/g) |
|---|---|---|---|---|---|
| URF-TAC | 10.86 ± 1.07 | 3 | 0.0346 | 20.02 | 111.19 ± 20.16 |
| URF-TAC:LAC | 14.09 ± 1.50 | 2 | 0.0334 | 20.75 | 122.42 ± 6.19 |

$C_{max}$: maximum concentration
$T_{max}$: time to $C_{max}$
$K_{el}$: elimination rate constant
$T_{1/2}$: half-life
$AUC_{(0-24)}$: area-under-the-curve between 0-24 hours The $C_{max}$ for URF-TAC:LAC was significantly higher (14.09 µg/g) compared to URF-TAC (10.86 µg/g) whereas $T_{max}$ was significantly lower (p<0.05) for 2 hours. This could perhaps as a result of a greater dissolved concentration, as seen in the in vitro supersaturation results. However, no significant differences in AUC-values (0-24 hr) were observed between the two URF formulations (p>0.05). The results indicated that the amorphous nature of the particles affects the rate of drug absorption. TAC in the URF-TAC:LAC was eliminated according to a biphasic pattern with distribution phase and elimination phase. The similar elimination pattern was also found in the URF-TAC The values of $K_{el}$ were not significantly different between the two URF-formulations (p>0.05). The decreasing TAC concentration in the lung for both URF formulations is a consequence of drug distribution and transport into the systemic circulation, as well as particle elimination from the lung. It can be seen clearly that the transfer of nanostructured aggregates (either amorphous or crystalline) from the lung into systemic circulation was likely in a sustained manner after 6 hr. The measured levels for both URF formulations at 48 hours were below the limit of quantification of the assay (determined to be1 µg/g).

Figure 9:
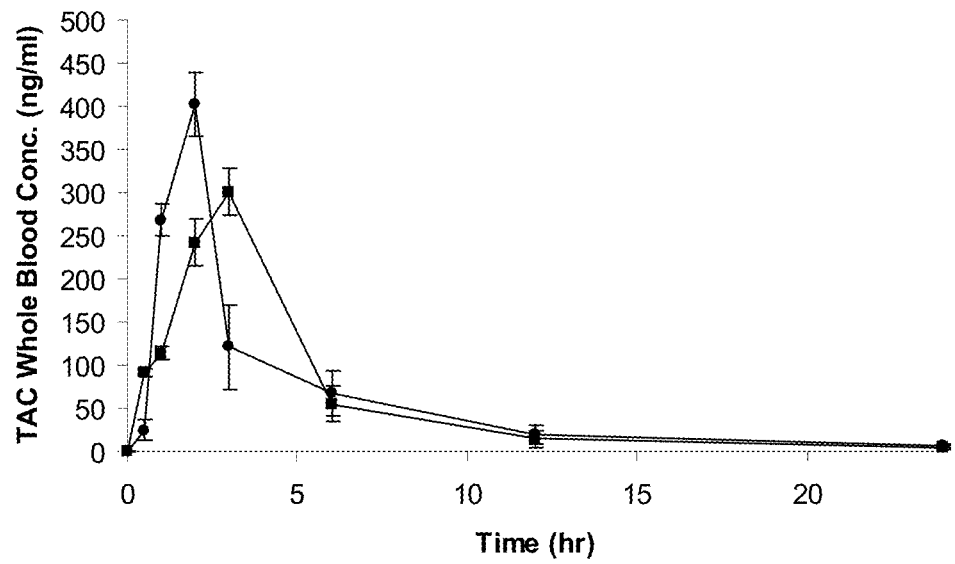
FIG. 9 is a graph that shows a comparison of mean whole-blood TAC concentration profiles of the URF formulations after a single inhalation administration. (□) Amorphous URF composition TAC:lactose (1:1) and (■) Crystalline URF composition TAC alone.
Figure 10A:
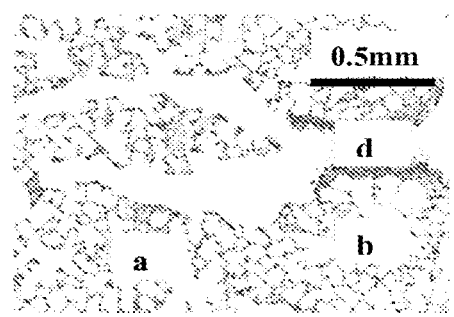
FIG. 10A: Lung tissue histology from TAC:LAC active group, day 7.
Figure 10B:
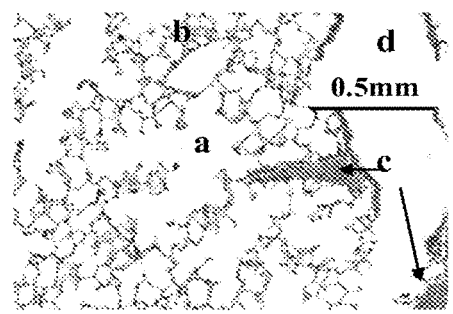
FIG. 10B: Lung tissue histology from TAC:LAC active group, day 14.
Figure 10C:
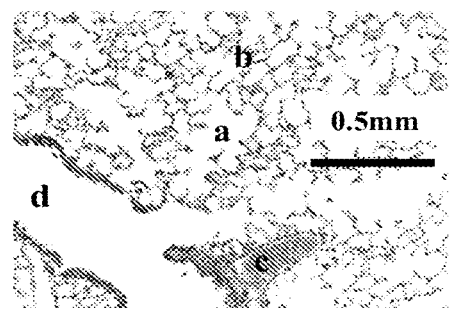
FIG. 10C: Lung tissue histology from LAC only control group, day 7.
Figure 10D:
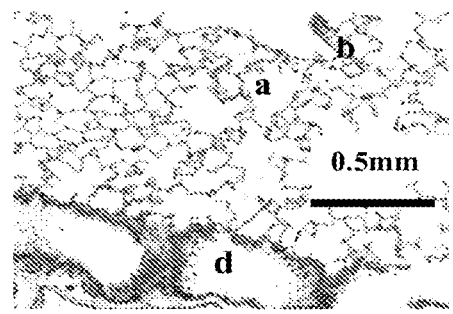
FIG. 10D: Lung tissue histology from LAC only control group, day 14 (Notes on histology: a: alveolar spaces; b: capillaries; c: lymph tissue; and d: arterioles with red blood cells present; (20× magnification)).

The systemic in vivo pharmacokinetic of drug absorption from the lungs was investigated in mice. FIG. 9 shows a comparison of mean whole blood concentration-time profiles from each formulation, and the calculated pharmacokinetic parameters following pulmonary administration are presented in Table 6.

TABLE 6

In vivo pharmacokinetic parameters for the whole-blood concentrations of the URF formulations following the pulmonary administration.

| Formulation | $C_{max}$ (ng/mL) | $T_{max}$ (hrs) | $K_{el}$ (hrs$^{-1}$) | $T_{1/2}$ (hrs) | $AUC_{(0-24)}$ (ng · hr/mL) |
|---|---|---|---|---|---|
| URF-TAC | 300.67 ± 27.04 | 3 | 0.123 | 5.63 | 1324.35 ± 318.07 |
| URF-TAC:LAC | 402.11 ± 35.99 | 2 | 0.115 | 6.02 | 1235.66 ± 65.86 |

$C_{max}$: maximum concentration
$T_{max}$: time to $C_{max}$
$K_{el}$: elimination rate constant
$T_{1/2}$: half-life
$AUC_{(0-24)}$: area-under-the-curve between 0-24 hours The whole blood concentration profile of each formulation has a similar absorption pattern, for example, $T_{max}$, compared to the lung concentration profiles (FIG. 8). However, both URF formulations demonstrated substantially lower TAC concentrations in the blood than was seen in the lung tissue. The whole blood profiles following pulmonary dosing of URF-TAC:LAC and URF-TAC had peak concentrations of 402.11 ng/mL at 2 hr and 300.67 ng/mL at 3 hr, respectively, before concentrations decreased. The $AUC_{(0-24)}$ (1235.66 ng·hr/mL) of the URF-TAC:LAC processed by URF is slightly lower than that of the URF-TAC (1324.35 ng·hr/mL), although there is no statistical difference (p>0.05). The levels of TAC decreased rapidly for URF-TAC:LAC with the last time point with a detectable levels occurring at 24 h, while URF-TAC declined in a similar but slower manner (no significant difference in the $K_{el}$ values (p>0.05)). Whole blood concentrations of TAC were below the limit of quantification for both formulations at 48 hours. The systemic and lung concentrations observed after nebulization of both URF formulations in mice suggest that a substantial lung and systemic exposure to TAC can be achieved in either amorphous nanostructed aggregates or crystalline nanostructed aggregates produced by URF. The observation that either amorphous or crystalline particles produced high systemic concentrations may suggest that high surface area was an important factor. High supersaturation, as a result of delivering amorphous particles in URF-TAC:LAC, correlated with faster absorption rates in both blood and lung tissue as compared to crystalline particles in URF-TAC. Use of supersaturated state in the lungs has not been previously studied yet. However, it has been demonstrated to enhance transdermal and oral absorption of poorly soluble drugs [37-39]. The in vivo data reported by Yamashita et al. [37] showed a high and extended systemic absorption of TAC following oral administration of amorphous solid dispersions with HPMC in beagle dogs. In the Yamashita et al. study, the solid dispersion of TAC with HPMC was prepared by solvent evaporation and was also shown to supersaturate in 0.1N HCl up to 25-times in 2 hours, and this level was maintained for over 24 hours. In our study, supersaturation of TAC from URF-TAC:LAC showed no effect on the extent of drug absorption in both lung tissue and systemic circulation. This can be explained by the fact that supersaturation occurred over a short period of time for the absorption phase and then TAC concentration was rapidly decreased in the elimination phase.

High surface area, nanostructured aggregates containing amorphous or crystalline nanoparticles of TAC were produced by the URF process and shown to be effectively aerosolized in an aqueous dispersion by nebulization. Inclusion of lactose prevented crystallization of TAC and resulted in amorphous powder. URF-TAC:LAC (i.e., amorphous nanostructured aggregates) demonstrated the ability to supersaturate in SLF compared to the URF-TAC (i.e., crystalline nanostructured aggregates). Dispersions of nebulized URF formulations exhibited high lung and systemic concentrations. The $AUC_{(0-24)}$ of the URF formulations which reflects the total amount of drug absorbed over the 24 h time period was not significantly different ($p>0.05$) for either lung or blood profiles. The results indicate that high drug absorption in lung tissue and blood following pulmonary administration was primarily due to high surface area of nanostructured aggregates from both formulations. The ability to achieve high solubility in the lungs translated to higher $C_{max}$ and lower $T_{max}$ values based on results of the in vivo studies. We have demonstrated that nanoparticles of TAC can be successfully delivered to the lungs without the use of polymers or surfactants.

Example 1. A formulation of tacrolimus (TAC) was produced using TAC and lactose (LAC) in ratio 1:1. The TAC:LAC 1:1 formulation was prepared using the ultra-rapid freezing (URF) process. The compositions were prepared by dissolving TAC and LAC at a 1:1 ratio and 0.75% solids in a 60/40 mixture of acetonitrile and water. The solution of drug and excipient was applied to the surface of a solid substrate, which is cooled using a cryogenic substrate maintained at −50° C. The frozen compositions were then collected and the solvent was removed by lyophilization using a VirTis Advantage Lyophilizer (VirTis Company, Inc. Gardiner, NY). The dried powders were stored at room temperature under vacuum.

Example 2. The composition in example 1 was characterized using X-ray powder diffraction (XRD). The XRD patterns of the powders were analyzed using a Philips 1710 x-ray diffractometer with a copper target and nickel filter (Philips Electronic Instruments, Mahwah, NJ). Each sample was measured from 5 to 45 2θ degrees using a step size of 0.05 2θ degrees and a dwell time of one second. The composition is amorphous.

Example 3. The composition in example 1 was characterized using BET specific surface area analysis. Specific surface area was measured using a Nova 2000 v 6.11 instrument (Quantachrome Instruments, Boynton Beach, FL). A known weight of powder was added to a 12 mm Quantachrome bulb sample cell and degassed for a minimum of 3 hours. The data recorded were then analyzed according to BET theory using NOVA Enhanced Data Reduction Software v. 2.13. The results showed that the composition has a BET specific surface area of 25.9 $m^2/g$, compared to 0.53 $m^2/g$ for unprocessed TAC.

Example 4. The composition in example 1 was characterized using scanning electron microscopy (SEM) in order to visualize the morphology of the particles produced. A Hitachi S-4500 field emission scanning electron microscope (Hitachi High-Technologies Corp., Tokyo, Japan) was used to obtain SEM micrographs of the powder samples. Samples were mounted on conductive tape and sputter coated using a K575 sputter coater (Emitech Products, Inc. Houston, TX) with gold/palladium for 30 sec. An acceleration voltage of 5-15 kV was used to view the images. The results of the SEM characterization of the powders showed highly porous nanostructured aggregates of TAC/LAC. The micrograph at high magnification revealed that the aggregates were composed of interconnected nanoparticles with a diameter of approximately 100-200 nm.

Example 5. The composition in example 1 was tested for its dissolution characteristics at sink conditions (defined here as 59% of equilibrium solubility in the dissolution medium) below the equilibrium solubility of TAC. Dissolution testing at conditions below equilibrium solubility was performed on the TAC:LAC formulation using a United States Pharmacopoeia (USP) 27 Type 2 dissolution apparatus (Vankel VK6010 Dissolution Tester with a Vanderkamp VK650A heater/circulator, Varian, Inc. Palo Alto, CA). Powder samples (0.4 mg TAC) equivalent to approximately 59% of the equilibrium solubility (6.8 μg/mL) were added to 100 mL of modified simulated lung fluid (SLF) with 0.02% DPPC as the dissolution medium. The dissolution medium was maintained at 37.0±0.2° C. and stirred at a constant rate of 100 RPM. Samples (1 mL) were withdrawn at 10, 20, 30, 60, and 120 minute time points, filtered using a 0.45 μm GHP Acrodisc filter (VWR, Inc. Westchester, PA), and analyzed using a Shimadzu LC-10 liquid chromatograph (Shimadzu Corporation, Kyoto, Japan) equipped with an Altech ODS-2, 5 μm C18 column (Altech Associates, Deerfield, IL). The mobile phase consisted of a 70:30 (v/v) ACN:water mixture, using a flow rate of 1 mL/min. The maximum absorbance was measured at wavelength λ=214 nm. The results of the dissolution testing below equilibrium solubility are shown in the Table 7:

| Time (min) | % Tacrolimus Dissolved |
|---|---|
| 0 | 0 |
| 10 | 41 |
| 20 | 59 |
| 30 | 73 |
| 60 | 82 |
| 120 | 94 |

Example 6. The composition in example 1 was tested for its dissolution characteristics under supersaturated conditions. Supersaturated dissolution profiles were generated according to the method described in example 5, using the small volume dissolution apparatus equipped with a paddle stirring mechanism. The drug formulation was weighed to correspond to approximately 15-times the aqueous crystalline solubility of TAC in 100 mL of the modified simulated lung fluid with 0.02% DPPC. Paddle speed and bath temperature were maintained at 100 RPM and 37.0° C., respectively. An aliquot (1 mL) was removed from the small volume vessel at 10, 20, 30, and 60 minutes, then at 2, 4, and 24 hours. Each aliquot was filtered through a 0.2 μm nylon filter, and a 0.5 mL aliquot of each filtered solution was immediately mixed with 1 mL of acetonitrile (to ensure no re-crystallization of drug previously dissolved at 37° C.). The samples were analyzed for TAC concentration using the same HPLC procedure described in example 5. The results for the supersaturated dissolution tests are shown below, Table 8.

TABLE 8

| Time (min) | Relative TAC Conc. (C/Ceq) |
|---|---|
| 0 | 0 |
| 10 | 5.3 |
| 20 | 6.9 |
| 30 | 9.7 |
| 60 | 10.6 |
| 120 | 6.7 |
| 240 | 3.1 |
| 1440 | 1.1 |

Example 7. The composition in example 1 was tested for its performance in vivo in the mouse, using pulmonary administration of the composition in example 1. Pulmonary dosing of the formulation was performed in healthy ICR mice (Harlan Sprague Dawley, Indianapolis, IN). The study protocol was approved by the Institutional Animal Care and Use Committee (IACUC) at the University of Texas at Austin, and all animals were maintained in accordance with the American Association for Accreditation of Laboratory Animal Care. Mice were acclimated in the restraint tubes (Battelle, Columbus, OH) for 10-15 min/day for 2 days prior to dosing. A small animal dosing apparatus for inhalation was used to dose the mice for the study. The dosing apparatus was designed to hold up to 4 mice per dosing time point. The dosing apparatus consists of a small volume hollow tube with dimensions of 20×4.5 cm with four 1.75 cm adapter holes drilled at 7 cm intervals, in order to accept rodent restraint tubes from the Battelle toxicology testing unit. The composition of Example 1 was re-dispersed in water (10 mg/mL) followed by sonication for 1 min prior to dosing to prepare the nebulization suspension. Nebulization of 3 mL of prepared suspension was conducted using an Aeroneb® Professional micropump nebulizer for 10 min. After pulmonary dosing, the mice were removed from the dosing apparatus and rested for 15 min. Two mice were sacrificed at each time point by $CO_2$ narcosis (0.5, 1, 2, 3, 6, 12, 24, and 48 hours). Whole blood (1 mL aliquots) was obtained via cardiac puncture and analyzed using a PRO-Trac II FK 506 ELISA, following the procedure detailed in the PRO-Trac II FK 506 ELISA assay kit literature (Diasorin, Inc. Stillwater, OK). In addition, necropsy was performed on each mouse to extract lung tissue. Samples were stored at −20° C. until assayed. TAC concentration in the lung tissue was determined by using the HPLC method described in example 5. The results for the blood and lung tissue TAC concentrations are shown in Tables 9 and 10:

TABLE 9

TAC Whole Blood Concentrations following Pulmonary Dosing:

| Time (hr) | Mouse 1 TAC Conc. (ng/mL blood) | Mouse 2 TAC Conc. (ng/mL blood) | Average TAC Conc. (ng/mL blood) |
|---|---|---|---|
| 0 | 0 | 0 | 0 |
| 0.5 | 33.68 | 16.22 | 24.95, SD = 8.73 |
| 1 | 254.97 | 281.42 | 268.20, SD = 13.22 |
| 2 | 427.56 | 376.65 | 402.11, SD = 25.45 |
| 3 | 155.70 | 86.72 | 121.21, SD = 31.50 |
| 6 | 49.56 | 86.65 | 68.11, SD = 18.55 |
| 12 | 26.25 | 11.13 | 18.68, SD = 7.56 |
| 24 | 5.88 | 8.05 | 6.97, SD = 1.09 |
| 48 | N/A | N/A | N/A |

TABLE 10

TAC Lung Tissue Concentrations following Pulmonary Administration:

| Time (hr) | Mouse 1 TAC Conc. (µg/g lung weight) | Mouse 2 TAC Conc. (µg/g lung weight) | Average TAC Conc. (µg/g lung weight) |
|---|---|---|---|
| 0 | 0 | 0 | 0 |
| 0.5 | 7.31 | 9.05 | 8.06, SD = 0.99 |
| 1 | 11.41 | 12.27 | 10.10, SD = 2.09 |
| 2 | 13.59 | 14.14 | 14.09, SD = 1.50 |
| 3 | 6.73 | 8.61 | 8.22, SD = 1.18 |
| 6 | 4.46 | 4.19 | 5.02, SD = 1.00 |
| 12 | 5.95 | 6.11 | 4.80, SD = 1.42 |
| 24 | 3.29 | 2.93 | 3.51, SD = 0.59 |
| 48 | N/A | N/A | N/A |

Example 8. A formulation of tacrolimus (TAC) was produced using TAC and glucose (GLU) in ratio 1:1. The TAC:GLU 1:1 formulation was prepared using the ultra-rapid freezing (URF) process. The composition was prepared by dissolving TAC and GLU at a 1:1 ratio and 0.75% solids in a 60/40 mixture of acetonitrile and water. The solution of drug and excipient was applied to the surface of a solid substrate, which is cooled using a cryogenic substrate maintained at −50° C. The frozen compositions were then collected and the solvent was removed by lyophilization using a VirTis Advantage Lyophilizer (VirTis Company, Inc. Gardiner, NY). The dried powders were stored at room temperature under vacuum. The result of XRD characterization (following the procedure in example 2) is that the formulation is amorphous. The result of SEM (following the procedure in example 4) is that the morphology is nano-structured aggregates with small primary particles consisting of TAC and GLU with primary particle sizes of about 100-300 nm.

Example 9. A formulation of tacrolimus (TAC) was produced using TAC and mannitol (MAN) in ratio 1:1. The TAC:MAN 1:1 formulation was prepared using the ultra-rapid freezing (URF) process. The composition was prepared by dissolving TAC and MAN at a 1:1 ratio and 0.75% solids in a 60/40 mixture of acetonitrile and water. The solution of drug and excipient was applied to the surface of a solid substrate, which is cooled using a cryogenic substrate maintained at −50° C. The frozen compositions were then collected and the solvent was removed by lyophilization using a VirTis Advantage Lyophilizer (VirTis Company, Inc. Gardiner, NY). The dried powders were stored at room temperature under vacuum. The result of XRD characterization (following the procedure in example 2) is that the composition is amorphous. The result of SEM (following the procedure in example 4) is that the morphology is nano-structured aggregates with small primary particles consisting of TAC and MAN with primary particle sizes of about 100-200 nm.

Example 10. A formulation of tacrolimus (TAC) was produced using TAC and inulin (INL) in ratio 1:1. The TAC:INL 1:1 formulation was prepared using the ultra-rapid freezing (URF) process. The composition was prepared by dissolving TAC and INL at a 1:1 ratio and 0.75% solids in a 60/40 mixture of acetonitrile and water. The solution of drug and excipient was applied to the surface of a solid substrate, which is cooled using a cryogenic substrate maintained at −50° C. The frozen compositions were then collected and the solvent was removed by lyophilization using a VirTis Advantage Lyophilizer (VirTis Company, Inc. Gardiner, NY). The dried powders were stored at room temperature under vacuum. The result of XRD characterization (following the procedure in example 2) is that the formulation is amorphous. The result of SEM visualization (following the procedure in example 4) is that the formulation's morphology is nanostructured aggregates with small primary particles consisting of TAC and INL with primary particle sizes of about 100-200 nm.

Example 11. In order to evaluate the rodent dosing apparatus used in these studies, an in vitro and in vivo study of the apparatus was conducted using itraconazole (ITZ). An animal dosing inhalation apparatus was constructed, consisting of a hollow tube (20×4.5 cm, nominal wall thickness of 0.4 cm) with four 1.75 cm adapter holes drilled at 7 cm intervals (2 holes on each side). The adapter holes were constructed to accept rodent restraint tubes from the Battelle toxicology testing unit. A ITZ colloidal suspension was nebulized into the apparatus for 5 min using a micro-pump nebulizer. Atomized droplets containing ITZ were driven into the chamber at a flow rate of 1 mL/min. ITZ concentrations were measured in vitro at the 4 adapter ports, and in vivo from the lungs of male outbred ICR mice in the appropriate mice restraining tubes at the adapter ports. The in vitro results showed that ITZ concentrations (S.D.) were 3.35 (0.75) μg/mL at the adapter ports following 5 min nebulization. In vivo results showed that lung concentrations of ITZ were 32 (3.0) μg/g wet lung weight (n=8). This was found to be three times higher than had previously been determined using a restraint-free whole body exposure unit in the same strain of mouse with double the exposure time. High concentrations of ITZ are achieved in the rodent lung with low variability. A commercially available nebulizer can be used for short dosing periods that negate the need to use invasive and variable dosing techniques. The data for the in vivo mouse study is Table 11:

TABLE 11

ITZ Conc. in Lung Tissue.

| Mouse | ITZ Conc. in Lung Tissue (μg/g) |
|---|---|
| Mouse 1 | 13.5 |
| Mouse 2 | 15.9 |
| Mouse 3 | 18.6 |
| Mouse 4 | 19.2 |
| Mouse 5 | 22.7 |
| Mouse 6 | 21.6 |
| Mouse 7 | 20.2 |
| Mouse 8 | 18.3 |
| Average | 18.7, SD = 3.0 |

Example 12. The composition in example 1 was tested for its performance in vivo in the mouse model after multiple dosing. The dosing apparatus described in example 7 was used. Re-dispersion and dosing concentration described in example 7 was also used; however, dosing occurred once daily. Two groups of four mice were sacrificed by isoflurane inhalation after multiple dosing. One group of four received 6 doses, the other received 13 doses. Animals were sacrificed 24 hours after the last dose was administered and trough blood samples were taken. Whole blood and lung tissue samples were extracted and assayed as described in example 7. The results for the blood and lung tissue TAC concentrations are shown in Table 12 and 13.

TABLE 12

TAC Whole Blood Concentrations following Daily Pulmonary Dosing in Mice

| Day of Sacrifice | Avg. Blood Volume (mL) | Avg. TAC Conc. (ng/mL) | Amount of TAC in Blood (μg) |
|---|---|---|---|
| 7 | 2.4 | 2.39 | 0.0057 |
| 14 | 2.4 | 2.649 | 0.0064 |

TABLE 13

TAC Lung Concentrations following Daily Pulmonary Dosing in Mice

| Day of Sacrifice | Avg. Lung Weight (g) | Avg. TAC Conc. (μg/g) | Amount of TAC in Lung (μg) |
|---|---|---|---|
| 7 | 0.2205 | 7.19 | 1.585 |
| 14 | 0.2193 | 6.735 | 1.477 |

Example 13. Lung tissue from the study conducted in example 12 was subjected to histological examination. Lungs were inflated with 10% formalin solution after sacrifice, tied at the trachea, and extracted. Sections of the lungs were taken, stained, and embedded in paraffin wax. Along with the active dosing groups described in example 12, a control group dosed with lactose solution for 6 and 13 days was evaluated. No evidence of tissue damage was observed in either case. Images from microscopic evaluation are shown in FIG. 10A-10D.

Example 14. The composition in example 1 was tested for its performance in vivo in the rat model at a lowered dose in comparison to the dose in example 7. Pulmonary dosing of the formulation was performed in healthy Sprague Dawley rats (Harlan, Indianapolis IN). The study protocol was approved by the Institutional Animal Care and Use Committee (IACUC) at the University of Texas at Austin, and all animals were maintained in accordance with the American Association for Accreditation of Laboratory Animal Care. Rats were acclimated in the restraint tubes (Battelle, Columbus, OH) for 10-15 min/day for 2 days prior to dosing. A small animal dosing apparatus for inhalation was used to dose the rats for the study. The dosing apparatus was designed to hold up to 4 rats per dosing time point. The dosing apparatus consists of a small volume hollow tube with dimensions of 2×4.5 cm with four 1.75 cm adapter holes drilled at 7 cm intervals and staggered on either side, in order to accept rodent restraint tubes from the Battelle toxicology testing unit. The composition of Example 1 was re-dispersed in water (1.1 mg/mL) followed by sonication for 1 min prior to dosing to prepare the nebulization suspension. Nebulization of 3 mL of prepared suspension was conducted using an Aeroneb® Professional micropump nebulizer for 10 min. After pulmonary dosing, the rats were removed from the dosing apparatus, rested for 1 hour, then euthanized by CO2 narcosis. Whole blood aliquots were extracted and assayed as described in example 7. The results for the whole blood TAC concentrations are shown in Table 14

TABLE 14

TAC Whole Blood Concentrations following Pulmonary Administration at a Lowered Dose in Rats

| Rat | TAC Conc. in Blood (ng/mL) |
|---|---|
| Rat 1 | 7.20 |
| Rat 2 | 1.53 |
| Rat 3 | 4.42 |
| Rat 4 | 2.50 |
| Average | 3.91, SD = 2.5 |

Example 15. The composition in example 1 was tested for its performance in vivo in the rat after multiple dosing. The dosing apparatus described in example 14 was used. Re-dispersion and dosing concentration described in example 14 was also used; however, dosing occurred once daily. Eight rats were sacrificed by isoflurane inhalation after 21 doses. Animals were sacrificed 24 hours after the last dose was administered and trough blood samples were taken. Whole blood samples were assayed as described in example 14. The results for the whole blood TAC concentrations are shown in Table 15.

TABLE 15

TAC Whole Blood Concentrations following 21 Days Continuous Pulmonary Administration at a Lowered Dose in Rats

| Rat | TAC Conc in Blood (ng/mL) |
|---|---|
| Rat 1 | 2.2096 |
| Rat 2 | 1.8193 |
| Rat 3 | 1.4874 |
| Rat 4 | 2.7917 |
| Rat 5 | 1.4187 |
| Rat 6 | 1.4075 |
| Rat 7 | 1.4874 |
| Rat 8 | 1.3742 |
| Average | 1.75, SD = 0.5 |

Example 16. The composition in example 1 was tested for its performance in vivo in a rat lung transplant model at the lowered dose used in example 14. Pulmonary dosing of the formulation was performed in healthy, lung transplanted Sprague Dawley rats (Harlan, Indianapolis IN). Surgery was performed to replace the left lung with a healthy left lung from the same species. Rats were given at least 7 days before dose was administered. The study protocol was approved by the Institutional Animal Care and Use Committee (IACUC) at the University of Texas Health Science Center in San Antonio, and all animals were maintained in accordance with the American Association for Accreditation of Laboratory Animal Care. Dosing was conducted as detailed in example 14; however, euthanasia was performed by tissue necropsy after isoflurane anesthesia. Whole blood aliquots were extracted from 3 transplanted rats for two time points and assayed as described in example 7. The results for the whole blood TAC concentrations at 6 and 12 hrs were 2.97±0.3 and 2.55±0.3 ng/mL, respectively. Right and left lung tissue samples were also harvested and analyzed for TAC from 3 transplanted rats at two time points content by liquid chromatography/mass spectrometry (LC/MS). Briefly, lung tissue was homogenized and proteins were precipitated to separate the analyte. Samples were spiked with an internal standard to assess and correct for extraction efficiency. The results for left (transplanted) lung TAC at 6 and 12 hrs were 319.8±80 and 160.4±46 ng/g, respectively. The results for right lung TAC concentration at 6 and 12 hrs were 125.0±5 and 62.6.4±17 ng/g, respectively.

Example 17. The composition in example 1 was tested for its performance in vivo in a rat lung transplant model described in example 16 at the lowered dose used in example 14. After sacrifice, lungs were extracted and sectioned into proximal airway and distal airway portions. These sections were analyzed for percent of total lung TAC according to mass by LC/MS according to example 16. The results for right proximal, right distal, left proximal, and left distal in 3 lung transplanted rats at the six hour time point were 4.0±6%, 49.3±4%, 33.6±4%, and 13.1±5% total TAC deposited, respectively. In a single non-transplanted rat in the same study, results for right proximal, right distal, left proximal, and left distal at the six hour time point were 2.6%, 49.0%, 25.1%, and 23.3% total TAC deposited, respectively.

Example 18. The composition in example 1 was tested for its in vitro performance in mixed lymphocyte culture (MLC) immune response analysis. This test is initiated by culturing bone marrow cells from a transplant host with cells from a transplant donor. Lymphocyte proliferation in this culture was assessed for histocompatibility without tacrolimus, after the addition of Prograf® dissolved in ethanol, and after the addition of TAC:LAC composition dispersed in water. Percent inhibition was determined relative to the culture lymphocyte count without the presence of tacrolimus. An average inhibition was calculated after four iterations. It was found that at equivalent doses, Prograf® dissolved in ethanol inhibited lymphocyte proliferation by 45%, while TAC: LAC dispersed in water inhibited proliferation by 86%.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CAB ABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Hooks, M. A. (1994) Tacrolimus, A New Immunosuppressant—A review of the literature. Ann. Pharmacother. 28, 501-511.
Waldrep, J. C. (1998) New aerosol drug delivery systems for the treatment of immune-mediated pulmonary diseases. Drugs of Today 34, 549-561.
Loser, K., Balkow, S., Higuchi, T., Apelt, J., Kuhn, A., Luger, T. A., and Beissert, S. (2006) FK506 Controls CD40L-Induced Systemic Autoimmunity in Mice 126, 1307-1315.
Tacca, M. D. (2004) Prospects for personalized immunosuppression: pharmacologic tools—a review. Transplant. Proc. 36, 687-689.
Jain, A. B., and Fung, J. J. (1996) Cyclosporin and tacrolimus in clinical transplantation—A comparative review. Clinical Immunotherapeutics 5, 351-373.
Tamura, S., Tokunaga, Y., Ibuki, R., Amidon, G. L., Sezaki, H., and Yamashita, S. (2003) The Site-Specific Transport and Metabolism of Tacrolimus in Rat Small Intestine. J Pharmacol Exp Ther 306, 310-316.
Venkataramanan R, J. A., Warty V W, et al. (1991) Pharmacokinetics of FK506 following oral administration: a comparison of FK506 and cyclosporine. Transplant. Proc. 23, 931-933.
Venkataramanan, R., Swaminathan, A., Prasad, T., Jain, A., Zuckerman, S., Warty, V., McMichael, J., Lever, J., Burckart, G., and Starzl, T. (1995) Clinical pharmacokinetics of tacrolimus. Clin. Pharmacokinet. 29, 404-430.
Kawashima, Y. (2001) Nanoparticulate systems for improved drug delivery. Adv. Drug Deliv. Rev. 47, 1-2.
Grenha, A., Seijo, B., and Remunan-Lopez, C. (2005) Microencapsulated chitosan nanoparticles for lung protein delivery. Eur. J. Pharm. Sci. 25, 427-437.
Taylor, K. M. G., and McCallion, O. N. M. (1997) Ultrasonic nebulisers for pulmonary drug delivery. Int. J Pharm. 153, 93-104.
Martinet, Y., Pinkston, P., Saltini, C., Spurzem, J., Muller-Quernheim, J., and Crystal, R. G. (1988) Evaluation of the in vitro and in vivo effects of cyclosporine on the lung T-lymphocyte alveolitis of active pulmonary sarcoidosis. Am. Rev. Respir. Dis. 138, 1242-1248.
McConville, J. T., Overhoff, K. A., Sinswat, P., Vaughn, J. M., Frei, B. L., Burgess, D. S., Talbert, R. L., Peters, J. I., Johnston, K. P., and Williams, R. O. (2006) Targeted high lung concentrations of itraconazole using nebulized dispersions in a murine model. Pharmaceutical Research 23, 901-911.
Steckel, H., Eskandar, F., and Witthohn, K. (2003) The effect of formulation variables on the stability of nebulized aviscumine. Int. J Pharm. 257, 181-194.
Fu, J., Fiegel, J., Krauland, E., and Hanes, J. (2002) New polymeric carriers for controlled drug delivery following inhalation or injection. Biomaterials 23, 4425-4433.
Brambilla, G., Ganderton, D., Garzia, R., Lewis, D., Meakin, B., and Ventura, P. (1999) Modulation of aerosol clouds produced by pressurised inhalation aerosols. Int. J Pharm. 186, 53-61.
Keenan, R. J., Zeevi, A., Iacono, A. T., Spichty, K. J., Cai, J. Z., Yousem, S. A., Ohori, P., Paradis, I. L., Kawai, A., and Griffith, B. P. (1995) Efficacy of inhaled cyclosporine in lung transplant patients with refractory rejection: correlation of intragraft cytokine gene expression with pulmonary function and histologic characteristics. Surgery 118, 385-392.
Keenan, R. J., Duncan, A. J., Yousem, S. A., Zenati, M., Schaper, M., Dowling, R. D., Alarie, Y., Burckart, G. J., and Griffith, B. P. (1992) Improved immunosuppression with aerosolized cyclosporine in experimental pulmonary transplantation. Transplantation 53, 20-25.
Blot, F., Tavakoli, R., Sellam, S., Epardeau, B., Faurisson, F., Bernard, N., Becquemin, M.-H., Frachon, I., Stern, M., Pocidalo, J.-J., Carbon, C., Bisson, A., and Caubarrere, I. (1995) Nebulized cyclosporine for prevention of acute pulmonary allograft rejection in the rat: Pharmacokinetic and histologic study. J. Heart Lung Transplant. 14, 1162-1172.
Waldrep, J. C., Arppe, J., Jansa, K. A., and Vidgren, M. (1998) Experimental pulmonary delivery of cyclosporin A by liposome aerosol. Int. J Pharm. 160, 239-249.
Rogers T L, Nelsen A C, Hu J, Johnston K P, Williams III R O. (2002) A novel particle engineering technology to enhance dissolution of poorly water soluble drugs: spray-freezing into liquid. Eur. J. Pharm. Biopharm. 54: 271-280.
Rogers T L, Hu J, Yu Z, Johnston K P, Williams III RO. (2002) A novel particle engineering technology: spray-freezing into liquid. Int. J Pharm. 242: 93-100.
Rogers T L, Nelsen A C, Sarkari M, Young T J, Johnston K P, Williams III RO. (2003) Enhanced aqueous dissolution of a poorly water soluble drug by novel particle engineering technology: Spray-freezing into liquid with atmospheric freeze-drying. Pharm. Res. 20: 485-493.
Rogers T L, Overhoff K A, Shah P, Johnston K P, Williams III RO. (2003) Micronized powders of a poorly water soluble drug produced by a spray-freezing into liquid-emulsion process. Eur. J. Pharm. Biopharm. 55: 161-172.
Hu, J., Johnston, K. P., Williams III, R. O. (2004) Stable amorphous danazol nanostructured powders with rapid dissolution rates produced by spray freezing into liquid. Drug Dev. Ind. Pharm. 30: 695-704.

Yu Z, Rogers T L, Hu J, Johnston K P, Williams III RO. (2002) Preparation and characterization of microparticles containing peptide produced by a novel process: spray freezing into liquid. Eur. J. Pharm. Biopharm. 54: 221-228.

Evans, J. C., Scherzer, B. D., Tocco, C. D., Kupperblatt, G. B., Becker, J. N., Wilson, D. L., Saghir, S., and Elder, E. J.: Preparation of nanostructured particles of poorly water soluble drugs via a novel ultrarapid freezing technology. In Polymeric Drug Delivery Ii: Polymeric Matrices and Drug Particle Engineering, vol. 924, pp. 320-328, 2006.

Overhoff, K. A., Engstrom, J. D., Chen, B., Scherzer, B. D., Milner, T. E., Johnston, K. P., and III, R. O. W. Novel Ultra-rapid Freezing Particle Engineering Process for Enhancement of Dissolution Rates of Poorly Water Soluble Drugs. in press. 2006.

Davies, N. M., and Feddah, M. R. (2003) A novel method for assessing dissolution of aerosol inhaler products. Int. J Pharm. 255, 175-187.

D. J. Van Drooge, W. L. J. H., H. W. Frijlink., (2004) Incorporation of lipophilic drugs in sugar glasses by lyophilization using a mixture of water and tertiary butyl alcohol as solvent. J Pharm. Sci. 93, 713-725.

Eriksson, J. H. C., Hinrichs, W. L. J., de Jong, G. J., Somsen, G. W., and Frijlink, H. W. (2003) Investigations into the Stabilization of Drugs by Sugar Glasses: III. The Influence of Various High-pH Buffers. Pharm. Res. 20, 1437-1443.

Bosquillon, C., Lombry, C., Preat, V., and Vanbever, R. (2001) Influence of formulation excipients and physical characteristics of inhalation dry powders on their aerosolization performance. J. Control. Release 70, 329-339.

Wierik, H., and Diepenmaat, P. (2002) Formulation of lactose for inhaled delivery systems. Pharm. Tech. Eur. 11, 1-5.

de Boer, A. H., Gjaltema, D., Hagedoorn, P., and Frijlink, H. W. (2002) Characterization of inhalation aerosols: a critical evaluation of cascade impactor analysis and laser diffraction technique. Int. J Pharm. 249, 219-231.

Zeng, X. M., Martin, G. P., and Marriott, C. (1995) The controlled delivery of drugs to the lung. Int. J Pharm. 124, 149-164.

Miller, F. J., Mercer, R. R., and Crapo, J. D. (1993) Lower Respiratory-Tract Structure of Laboratory-Animals and Humans—Dosimetry Implications. Aerosol Sci. Tech. 18, 257-271.

Yamashita, K., Nakate, T., Okimoto, K., Ohike, A., Tokunaga, Y., Ibuki, R., Higaki, K., and Kimura, T. (2003) Establishment of new preparation method for solid dispersion formulation of tacrolimus. Int. J Pharm. 267, 79-91.

Gao, P., Guyton, M. E., Huang, T., Bauer, J. M., Stefanski, K. J., and Lu, Q. (2004) Enhanced Oral Bioavailability of a Poorly Water Soluble Drug PNU-91325 by Supersaturatable Formulations. Drug Dev. Ind. Pharm. 30, 221-229.

Iervolino, M., Cappello, B., Raghavan, S. L., and Hadgraft, J. (2001) Penetration enhancement of ibuprofen from supersaturated solutions through human skin. Int. J Pharm. 212, 131-141.

What is claimed is:

1. A method of making a pharmaceutical powder, the powder comprising porous, nanostructured aggregates comprising tacrolimus and a carbohydrate, the nanostructured aggregates being composed of branched and interconnected nanorods, wherein the powder is a) free of cyclosporine, b) free of surfactants and c) free of ethanol, propylene glycol and polyethylene glycol, wherein the method comprises:
   i) mixing tacrolimus and carbohydrate with a solvent;
   ii) ultra-rapid freezing the mixture; and
   iii) removing the solvent to provide the pharmaceutical powder.

2. The method of claim 1, wherein the nanostructured aggregates have a surface area of greater than 10 $m^2/g$.

3. The method of claim 1, wherein the nanostructured aggregates have a surface area of greater than 20 $m^2/g$.

4. The method of claim 1, wherein the nanostructured aggregates have a surface area of greater than 30 $m^2/g$.

5. The method of claim 1, wherein the nanostructured aggregates are provided in a form for immediate release, extended release, pulsed release, delayed release, controlled release or combinations thereof.

6. The method of claim 1, wherein the powder further comprises an organic salt, amino acid, peptide, or protein.

7. The method of claim 1, wherein the carbohydrate is mannitol, raffinose, lactose, maltodextrin, trehalose or combinations thereof.

8. The method of claim 7, wherein the carbohydrate is lactose.

9. The method of claim 1, wherein the powder is positioned in a nebulizer, an air-jet nebulizer, an ultrasonic nebulizer, a metered dose inhaler, a dry powder inhalation device or a micro-pump nebulizer.

* * * * *